US008772454B2

(12) United States Patent
Matz et al.

(10) Patent No.: US 8,772,454 B2
(45) Date of Patent: Jul. 8, 2014

(54) ISOLATION AND CHARACTERIZATION OF NOVEL GREEN FLUORESCENT PROTEINS FROM COPEPODS

(75) Inventors: Mikhail V. Matz, Austin, TX (US); Marguerite E. Hunt, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 70 days.

(21) Appl. No.: 13/256,915

(22) PCT Filed: Mar. 10, 2010

(86) PCT No.: PCT/US2010/026755
§ 371 (c)(1),
(2), (4) Date: Nov. 28, 2011

(87) PCT Pub. No.: WO2010/107639
PCT Pub. Date: Sep. 23, 2010

(65) Prior Publication Data
US 2012/0071631 A1     Mar. 22, 2012

Related U.S. Application Data

(60) Provisional application No. 61/162,112, filed on Mar. 20, 2009.

(51) Int. Cl.
*C07K 14/435* (2006.01)
(52) U.S. Cl.
USPC ......................................................... 530/350
(58) Field of Classification Search
None
See application file for complete search history.

(56) References Cited

U.S. PATENT DOCUMENTS

| | | | |
|---|---|---|---|
| 5,625,048 | A | 4/1997 | Tsien et al. |
| 2004/0086968 | A1 | 5/2004 | Evans |
| 2004/0154046 | A1 | 8/2004 | Yonekawa et al. |
| 2006/0166196 | A1 | 7/2006 | Iida et al. |
| 2009/0170073 | A1* | 7/2009 | Miyawaki et al. ................ 435/6 |

FOREIGN PATENT DOCUMENTS

| | | |
|---|---|---|
| KR | 1020030075820 A | 9/2003 |
| KR | 1020030081548 A | 10/2003 |
| WO | 9507643 A1 | 3/1995 |
| WO | WO 2004/058973 A1 * | 7/2004 |
| WO | WO 2004/111235 A1 * | 12/2004 |
| WO | 2010017639 A2 | 9/2010 |

OTHER PUBLICATIONS

GenBank Accession No. AY268076, Apr. 200, 2 pages.*
GenBank Accession No. AY268076, Apr. 2004, 2 pages.*
Alieva, Naila, et al., "Diversity and Evolution of Coral Fluorescent Proteins," PLOS One Jul. 2008, vol. 3, Issue 7, 12 pages.
Altschul, Stephen F., et al., "Basic Local Alignment Search Tool," J. Mol. Biol., (1990), 215:403-410.
Amsterdam, Adam, et al., "The Aequorea Victoria Green Fluorescent Protein Can be Used as a Reporter in Live Zebrafish Embryos," Developmental Biology, (1995), 171:123-129.
Baird, Geoffrey S., et al., "Biochemistry, Mutagenesis, and Oligomerization of DsRed, a Red Fluorescent Protein from Coral," PNAS, Oct. 24, 2000, vol. 97, No. 22, pp. 11984-11989.
Chudakov, Dmitriy M., et al., "Fluorescent Proteins as a Toolkit for In Vivo Imaging," Trends in Biotechnology, Dec. 2005, vol. 23, No. 12, pp. 605-613.
Deheyn, Dimitri D., et al., "Endogenous Green Fluorescent Protein (GFP) in Amphioxus," Biol. Bull., Oct. 2007, 213:95-100.
Evdokimov, Artem G., et al., "Structural Basis for the Fast Maturation of Arthropoda Green Fluorescent Protein," EMBO, (2006), vol. 7, No. 10, pp. 1006-1012.
Fleminger, Abraham, "New Calanoid Copepods of Pontella Dana and Labidocera Lubbock with Notes on the Distribution of the Genera in the Gulf of Mexico," Tulane Studies in Zoology, (1957), 5:19-34.
Gurskaya, Nadya G., et al., "A Colourless Green Fluorescent Protein Homologue from the Non-Fluorescent Hydromedusa Aequorea Coerulescens and its Fluorescent Mutants," Biochem J., (2003), 373:403-408.
Herring, Peter J., "Copepod Luminescence," Hydrobiologia, (1988), 168:183-195.
Himanen, Juha-Pekka, et al., "Recombinant Sickle Hemoglobin Containing a Lysine Substitution at Asp-85(a): Expression in Yeast, Functional Properties, and Participation in Gel Formation," Blood, (1997), 89:4196-4203.
Hirel, Ph.-Herve, et al., "Extent of N-Terminal Methionine Excision from *Escherichia coli* Proteins is Governed by the Side-Chain Length of the Penultimate Amino Acid," Proc. Natl. Acad. Sci., Nov. 1989, vol. 86, pp. 8247-8251.
Hochuli, Erich, "Large-Scale Chromatography of Recombinant Proteins," Journal of Chromatography, (1988), 444:293-302.
Huelsenbeck, John P., et al., "MRBAYES: Bayesian Inference of Phylogenetic Trees," Bioinformatics, (2001), vol. 17, No. 8, pp. 754-755.
Ikawa, Masahito, et al., A Rapid and Non-Invasive Selection of Transgenic Embryos Before Implantation Using Green Fluorescent Protein (GFP),: FEBS Letters, (1995), 375:125-128.
International Search Report and Written Opinion for PCT/US2010/026755, dated Nov. 26, 2010, 8 pages.
Land, Michael F., "The Functions of Eye and Body Movements in Labidocera and Other Copepods," J. Exp. Biol., (1988), 140:381-391.

(Continued)

*Primary Examiner* — David J Steadman
(74) *Attorney, Agent, or Firm* — Chainey P. Singleton; Edwin S. Flores; Chalker Flores, LLP

(57) ABSTRACT

The isolation and characterization of two protein isoforms collected green fluorescent copepods is described herein. The new *Pontella mimocerami* GFP-like isoforms pmimGFP1 and pmimGFP2 of the present invention are quick to mature and rapidly produce a fluorescent signal. The two isoforms are very similar in molar extinction coefficients (ME) with 105,000 $M^{-1}$ $cm^{-1}$ for pmimGFP1 and 103,000 $M^{-1}cm^{-1}$ for pmimGFP2, respectively. The relative brightness of these two new copepod GFP-like proteins is the highest measured for any isolated GFP-like protein.

9 Claims, 9 Drawing Sheets

(56) References Cited

OTHER PUBLICATIONS

Lippincott-Schwartz, Jennifer, et al., "Development and Use of Fluorescent Protein Markers in Living Cells," Science, Apr. 4, 2003, vol. 300, pp. 87-91.

Matz, Mikhail V., et al., "Evolution of Function and Color in GFP-Like Proteins," Green Fluorescent Protein: Properties, Applications and Protocols, Second Edition, (2006), pp. 139-161.

Matz, Mikhail V., et al., "Fluorescent Proteins from Nonbioluminescent Anthozoa Species," Nature Biotechnology, Oct. 1999, vol. 17, pp. 969-973.

Matz, Mikahil V., et al., "Family of the Green Fluorescent Protein: Journey to the End of the Rainbow," BioEssays, (2002), 24:953-959.

Miller, Jane C., et al., "Basic Statistical Methods for Analytical Chemistry Part I. Statistics of Repeated Measurements a Review," Analyst, Sep. 1988, vol. 113, pp. 1351-1356.

Ohtsuka, Susumu, et al., "Sexual Dimorphism in Calanoid Copepods: Morphology and Function," Hydrobiologia, (2001), pp. 441-466.

Shagin, Dmitry A., et al., "GFP-Like Proteins as Ubiquitous Metazoan Superfamily: Evolution of Functional Features and Structural Complexity," Molecular Biology, (2004), vol. 21, No. 5, pp. 841-850.

Shagin, Dmitry A., et al., "Regulation of Averago Length of Complex PCR Product," Nucleic Acids Research, (1999), vol. 27, No. 18, 3 pages.

Shaner, Nathan C., et al., "Improved Monomeric Red, Orange and Yellow Fluorescent Proteins Derived from *Discosoma* Sp. Red Fluorescent Protein," Nature Biothechnology, Nov. 2004, vol. 22, No. 12, pp. 1567-1572.

Shaner, Nathan C., et al., "Advances in Fluorescent Protein Technology," Journal of Cell Science, (2007), 120:4247-4260.

Sheen, Jen, et al., "Green-Fluorescent Protein as a New Vital Marker in Plant Cells," The Plant Journal, (1995), 8(5):777-784.

Shimomura, Osamu, et al., "Extraction, Purification and Properties of Awquorin, a Bioluminescent Protein from the Luminous Hydromedusan, Aequorea," J. Cell Comp. Physiol., (1962), 59:223-239.

Shine, J., et al., "Determinant of Cistron Specificity in Bacterial Ribosomes," Nature, Mar. 6, 1975, vol. 254, pp. 34-38.

Tavare, Simon, "Some Probabilistic and Statistical Problems in the Analysis of DNA Sequences," Lectures on Mathematics in the Life Sciences, (1986), vol. 17, pp. 57-85.

Tobias, John W., et al., "The N-End Rule in Bacteria," Science, Nov. 29, 1991, vol. 254, No. 5036, pp. 1374-1377.

Ward, William W., "Properties of the Coelenterate Green-Fluorescent Proteins," Bioluminescence and Chemiluminescence: Basic Chemistry and Analytical Applications, Academic Press, NY, (1981), pp. 235-242.

Yanushevich, et al., "A Strategy for the Generation of Non-Aggregating Mutants of Anthozoa Fluorescent Proteins," FEBS Letters, (2002), pp. 11-14.

* cited by examiner pmimGFP1 DS3 Pontella (SEQ. ID NO.: 1)

MPNMKLECRISGTMNGEEFELVGNGDGNTDEGRMTNKMKSTKGPLSFSPYLLSHVL
GYGYYHYATFPAGYENVYLHAMKNGGYSNTRTERYEDGGIISATFNYRYEGDKIIG
DFKVVGTGFPTNSIIFTDKIIKSNPTCEHIYPKADNILVNAYTRTWMLRDGGYYSAQV
NNHMHFKSAIHPTMLQNGGSMFTYRKVEELHTQTEVGIVEYQHVFKTPTAFA

*FIG. 6A* pmimGFP1 (SEQ. ID NO.: 2)

ATGCCCAACATGAAGCTTGAGTGCCGCATCTCCGGAACCATGAACGGAGAGGAG
TTTGAACTTGTTGGTAATGGAGATGGAAACACTGATGAGGGACGCATGACCAAC
AAGATGAAGTCCACCAAGGGACCTCTCTCCTTCTCTCCCTACTTGCTCTCCCATGT
TCTTGGCTATGGATACTACCACTATGCTACCTTCCCTGCTGGATATGAAAATGTCT
ACCTCCATGCCATGAAGAATGGAGGTTACTCTAACACAAGAACTGAGAGGTATG
AGGATGGAGGTATCATTTCTGCTACCTTCAACTACAGATATGAAGGAGACAAGA
TCATTGGGGACTTCAAGGTTGTTGGAACTGGATTCCCTACCAACAGCATCATCTT
CACTGACAAAATAATCAAGTCCAACCCTACCTGTGAGCACATCTACCCCAAGGCT
GACAATATTCTTGTGAATGCCTACACCAGAACCTGGATGCTTAGAGATGGTGGAT
ACTACTCTGCTCAGGTCAACAACCACATGCACTTCAAGAGTGCCATCCATCCCAC
CATGCTCCAGAATGGTGGATCCATGTTCACCTACAGAAAGGTTGAGGAGCTCCAC
ACACAAACTGAAGTTGGTATTGTTGAGTACCAGCATGTCTTCAAAACTCCAACTG
CTTTTGCT

*FIG. 6B* pmimGFP2 DS3 Pontella (SEQ. ID NO.: 3)

MPNMKLECRISGTMNGEEFKLVGAGEGNTDEGRMTNKVKSTKGPLPFSPYLLSHVL
GYGYYHYATFPAGYENVYLHAMKNGGYSNTRTERYEDGGIISATFNYRYEGDKIIG
DFKVVGTGFPTNSIIFTDKIIKSNPTCEHIYPKADNILVNAYTRTWMLRDGGYYSAQV
NNHMHFKSAIHPTMLQNGGSMFTYRKVEELHTQTEVGIVEYQHVFKRPTAFA

*FIG. 7A* pmimGFP2 (SEQ. ID NO.: 4)

ATGCCCAACATGAAGCTTGAGTGCCGTATCTCCGGAACCATGAACGGAGAGGAG
TTTAAACTTGTTGGTGCTGGAGAAGGAAACACTGATGAGGGACGCATGACCAAC
AAGGTGAAGTCCACCAAGGGACCTCTCCCCTTCTCTCCCTACTTGCTCTCTCACGT
TCTTGGCTATGGATACTACCACTATGCTACCTTCCCTGCTGGATATGAAAATGTCT
ACCTCCATGCCATGAAGAATGGAGGTTACTCCAACACCAGAACTGAGAGGTATG
AGGACGGAGGTATCATTTCTGCTACCTTCAACTACAGATATGAAGGAGACAAGA
TCATTGGAGACTTCAAGGTTGTTGGAACTGGATTCCCCACCAACAGCATCATCTT
CACTGACAAGATTATCAAGTCCAACCCTACCTGTGAGCACATATACCCCAAGGCT
GACAATATTCTTGTGAATGCCTACACCAGAACCTGGATGCTTAGAGATGGTGGAT
ACTACTCTGCTCAGGTCAACAACCACATGCACTTCAAGAGTGCCATCCATCCCAC
CATGCTCCAGAATGGTGGATCCATGTTCACCTACAGAAAGGTTGAGGAGCTCCAC
ACACAAACTGAAGTTGGTATTGTTGAGTACCAGCATGTCTTCAAGAGGCCAACTG
CTTTTGCT

*FIG. 7B*

Mutant 1 (pmimGFP1, K5E no histidine, SEQ. ID NO.: 5)

MPNMELECRISGTMNGEEFELVGNGDGNTDEGRMTNKMKSTKGPLSFSPYLLSHVLGYGYYHYATFPAGYENVYLHAMKNGGYSNTRTERYEDGGIISATFNYRYEGDKIIGDFKVVGTGFPTNSIIFTDKIIKSNPTCEHIYPKADNILVNAYTRTWMLRDGGYYSAQVNNHMHFKSAIHPTMLQNGGSMFTYRKVEELHTQTEVGIVEYQHVFKTPTAFA*

*FIG. 8A*

Mutant 1 (pmimGFP1, K5E no histidine, SEQ. ID NO.: 6)

ATGCCCAACATGGAGCTTGAGTGCCGCATCTCCGGAACCATGAACGGAGAGGAGTTTGAACTTGTTGGTAATGGAGATGGAAACACTGATGAGGGACGCATGACCAACAAGATGAAGTCCACCAAGGGACCTCTCTCCTTCTCTCCCTACTTGCTCTCCCATGTTCTTGGCTATGGATACTACCACTATGCTACCTTCCCTGCTGGATATGAAAATGTCTACCTCCATGCCATGAAGAATGGAGGTTACTCTAACACAAGAACTGAGAGGTATGAGGATGGAGGTATCATTTCTGCTACCTTCAACTACAGATATGAAGGAGACAAGATCATTGGGGACTTCAAGGTTGTTGGAACTGGATTCCCTACCAACAGCATCATCTTCACTGACAAAATAATCAAGTCCAACCCTACCTGTGAGCACATCTACCCCAAGGCTGACAATATTCTTGTGAATGCCTACACCAGAACCTGGATGCTTAGAGATGGTGGATACTACTCTGCTCAGGTCAACAACCACATGCACTTCAAGAGTGCCATCCATCCCACCATGCTCCAGAATGGTGGATCCATGTTCACCTACAGAAAGGTTGAGGAGCTCCACACACAAACTGAAGTTGGTATTGTTGAGTACCAGCATGTCTTCAAAACTCCAACTGCTTTTGCT

*FIG. 8B*

Mutant 3 (pmimGFP1, K5T, C8S, R9A no histidine, SEQ. ID NO.: 7)

MPNMTLESAISGTMNGEEFELVGNGDGNTDEGRMTNKMKSTKGPLSFSPYLLSHVL
GYGYYHYATFPAGYENVYLHAMKNGGYSNTRTERYEDGGIISATFNYRYEGDKIIG
DFKVVGTGFPTNSIIFTDKIIKSNPTCEIIYPKADNILVNAYTRTWMLRDGGYYSAQV
NNHMHFKSAIHPTMLQNGGSMFTYRKVEELHTQTEVGIVEYQHVFKTPTAFA*

FIG. 9A

Mutant 3 (pmimGFP1, K5T, C8S, R9A no histidine, SEQ. ID NO.: 8)

ATGCCCAACATGACGCTTGAGTCCGCCATCTCCGGAACCATGAACGGAGAGGAG
TTTGAACTTGTTGGTAATGGAGATGGAAACACTGATGAGGGACGCATGACCAAC
AAGATGAAGTCCACCAAGGGACCTCTCTCCTTCTCTCCCTACTTGCTCTCCCATGT
TCTTGGCTATGGATACTACCACTATGCTACCTTCCCTGCTGGATATGAAAATGTCT
ACCTCCATGCCATGAAGAATGGAGGTTACTCTAACACAAGAACTGAGAGGTATG
AGGATGGAGGTATCATTTCTGCTACCTTCAACTACAGATATGAAGGAGACAAGA
TCATTGGGGACTTCAAGGTTGTTGGAACTGGATTCCCTACCAACAGCATCATCTT
CACTGACAAAATAATCAAGTCCAACCCTACCTGTGAGCACATCTACCCCAAGGCT
GACAATATTCTTGTGAATGCCTACACCAGAACCTGGATGCTTAGAGATGGTGGAT
ACTACTCTGCTCAGGTCAACAACCACATGCACTTCAAGAGTGCCATCCATCCCAC
CATGCTCCAGAATGGTGGATCCATGTTCACCTACAGAAAGGTTGAGGAGCTCCAC
ACACAAACTGAAGTTGGTATTGTTGAGTACCAGCATGTCTTCAAAACTCCAACTG
CTTTTGCT

FIG. 9B

ISOLATION AND CHARACTERIZATION OF NOVEL GREEN FLUORESCENT PROTEINS FROM COPEPODS

STATEMENT OF FEDERALLY FUNDED RESEARCH

This invention was made with U.S. Government support under Contract No. R01 GM078247 awarded by the NIH. The government has certain rights in this invention.

CROSS-REFERENCE TO RELATED APPLICATIONS

This application is the National Stage of International Application No. PCT/US2010/026755, filed Mar. 10, 2010, which claims the benefit of U.S. Provisional Application No. 61/162,112 filed Mar. 20, 2009, which are incorporated herein by reference in its entirety.

INCORPORATION-BY-REFERENCE OF MATERIALS FILED ON COMPACT DISC

None.

TECHNICAL FIELD OF THE INVENTION

The present invention relates in general to the field of green fluorescent proteins (GFPs), and more particularly to the isolation and characterization of two novel GFP isoforms from a copepod species.

BACKGROUND ART

Without limiting the scope of the invention, its background is described in connection with the isolation and characterization of green fluorescent proteins (GFPs) from a marine copepod.

Green fluorescent proteins (GFPs) were originally isolated from the jellyfish *Aequorea victoria* and have a green fluorescence when exposed to blue light. WIPO patent WO/1995/007643 issued to Chalfir and Prasher (1995)[1] discloses a GFP from the jellyfish *A. Victoria* that retained its fluorescent properties when expressed in heterologous cells.

U.S. Pat. No. 5,625,048 issued to Tsien and Heim (1997)[2] teaches modifications in the sequence of *Aequorea* wild-type GFP to provide products having markedly different excitation and emission spectra from corresponding products from wild-type GFP. The modifications described included alteration in the ratio of the two main excitation peaks, fluorescence at shorter wavelengths, and the presence of only a single excitation peak.

US Patent Publication No. 20040086968 (Evans, 2004)[3] describes mutants of the GFP of *Aequorea victoria*. Specifically disclosed are nucleic acid molecules encoding mutant GFPs, the mutant GFPs encoded by these nucleic acid molecules, vectors and host cells comprising these nucleic acid molecules, and kits comprising one or more of the above as components. The invention also provided methods for producing these mutant GFPs. The fluorescence of these mutants is observable using fluorescein optics, making the mutant proteins of the present invention available for use in techniques such as fluorescence microscopy and flow cytometry using standard FITC filter sets.

DISCLOSURE OF THE INVENTION

The present invention describes novel green fluorescent copepods collected from the Atlantic Ocean. cDNA expression libraries were synthesized from the isolated mRNA to yield the genes responsible for the green fluorescence in the Pontellid copepods, similar to the GFP first isolated from the jellyfish *Aequorea victoria*.

In one embodiment the present invention discloses an isolated nucleic acid molecule comprising a nucleotide sequence that is at least 95% homologous to a SEQ. ID NO.: 2 or to a SEQ. ID NO.: 4. The nucleotide sequence described in the preferred embodiment is cloned from one or more RNA molecules isolated from one or more marine species, comprising of one or more Pontellids, jellyfish species, hydrozoans, anthozoans, corals, copepods, arthropods, crustaceans, chordates, cephalocordates, or any combinations thereof. In one aspect the nucleotide sequence encodes one or more functional proteins, and said nucleotide sequence is at least 95, 96, 97, 98 or 99% identical to a SEQ. ID NO.: 2 or to a SEQ. ID NO.: 4.

In another aspect the one or more functional proteins comprise one or more green fluorescent proteins, having a molar extinction coefficient of at least 100,000 $M^{-1}cm^{-1}$ and a quantum yield of at least 0.90. In yet another aspect the one or more green fluorescent proteins have an absorbance maximum between 480-490 nm and an emission maximum between 500-511 nm.

In another embodiment the present invention describes an isolated protein molecule comprising an amino acid sequence, wherein the amino acid sequence is at least 95% similar to a SEQ. ID NO.: 1 or to a SEQ. ID NO.: 3. In one aspect the protein molecule is a green fluorescent protein having a molar extinction coefficient of at least 100,000 $M^{-1}cm^{-1}$ and a quantum yield of at least 0.90. In an additional aspect the protein molecule comprises an amino acid sequence that is at least 95, 96, 97, 98 or 99% identical to a SEQ. ID NO.: 1 or to a SEQ. ID NO.: 3. In another aspect the protein molecule has an absorbance maximum between 480-490 nm and an emission maximum between 500-511 nm. In yet another aspect the protein molecule is isolated from one or more marine species, comprising of one or more Pontellids, jellyfish species, hydrozoans, anthozoans, corals, copepods, arthropods, crustaceans, chordates, cephalocordates, or any combinations thereof.

In yet another embodiment the present invention describes an expression vector comprising one or more nucleic acid sequences, wherein the nucleic acid sequence encodes one or more functional proteins. In one aspect the one or more nucleic acid sequences are at least 95% homologous to a SEQ. ID NO.: 2 or to a SEQ. ID NO.: 4. In another aspect the one or more encoded functional proteins have an amino acid sequence that is at least 95% similar to a SEQ. ID NO.: 1 or to a SEQ. ID NO.: 3. In yet another aspect the one or more nucleic acid sequences are cloned from one or more RNA molecules isolated from one or more marine species comprising one or more Pontellids, jellyfish species, hydrozoans, anthozoans, corals, copepods, arthropods, crustaceans, chordates, cephalocordates, or any combinations thereof. In an additional aspect the one or more encoded functional proteins comprise one or more green fluorescent proteins having a molar extinction coefficient of at least 100,000 $M^{-1}cm^{-1}$ and a quantum yield of at least 0.90, having an absorbance maximum between 480-490 nm and an emission maximum between 500-511 nm.

In a further embodiment the present invention discloses a host cell comprising a nucleic acid sequence wherein the nucleic acid sequence is at least 95% homologous to a SEQ. ID NO.: 2 or to a SEQ. ID NO.: 4; and encodes one or more functional proteins having an amino acid sequence that is at least 95% similar to a SEQ. ID NO.: 1 or to a SEQ. ID NO.:

3. In one aspect the host cell is selected from one or more microbial cells, mammalian cells, Z-cells, *E. coli* cells, eukaryotic cells, plasmids prokaryotic cells, or any combinations thereof.

One embodiment of the present invention is directed towards a method of expressing a green fluorescent protein in a host cell comprising the steps of: ligating one or more amplified nucleotides encoding the green fluorescent protein into a vector followed by inserting the vector into the host cell to express the green fluorescent protein. One aspect of the present invention describes a green fluorescent protein expressed by the method of the present invention.

Another embodiment of the present invention is a method of isolating one or more expressed green fluorescent proteins comprising the steps of: plating the one or more expressed green fluorescent proteins onto a culture plate, the culture plate is then incubated the culture at 37° C. for a period not less than 8 hours this is followed by selection and picking one or more green fluorescent colonies from the culture plate. The selected green fluorescent colonies are resuspended in water or a buffer; followed by plating onto a culture plate and incubation at room temperature for at least 48 hours. The green fluorescent colonies are resuspended in the buffer followed by sonication in the buffer on ice. The sonicated buffer solution is centrifuged and separated to yield a cleared lysate and a cellular debris. The expressed green fluorescent protein are isolated from the cleared lysate using metal-affinity chromatography, chromatography, affinity extraction, or other protein purification techniques. In one aspect the present invention described a green fluorescent protein isolated by the method of the present invention.

In a further embodiment the present invention describes a kit comprising one or more containers, wherein at least one of the containers comprises an isolated nucleic comprising a nucleotide sequence that is at least 95% homologous to a SEQ. ID NO.: 2 or to a SEQ. ID NO.: 4, an isolated protein molecule comprising an amino acid sequence, wherein the amino acid sequence is at least 95% identical to a SEQ. ID NO.: 1 or to a SEQ. ID NO.: 3, or both.

DESCRIPTION OF THE DRAWINGS

For a more complete understanding of the features and advantages of the present invention, reference is now made to the detailed description of the invention along with the accompanying figures and in which:

In FIG. 5B, the horizontal axis is time of illumination under the fluorescence microscope. In both figures, each point represents an average of three replicate measurements;

FIG. 6A shows the amino acid sequence of pmimGFP1 DS3 *Pontella* (SEQ. ID NO.: 1);

FIG. 6B shows the nucleic acid sequence of pmimGFP1 DS3 (SEQ. ID NO.: 2);

FIG. 7A shows the amino acid sequence of pmimGFP2 DS3 *Pontella* (SEQ. ID NO.: 3);

FIG. 7B shows the nucleic acid sequence of pmimGFP2 DS3 (SEQ. ID NO.: 4);

FIG. 8A shows the amino acid sequence of mutant 1: pmimGFP1 with K5E amino acid change (SEQ. ID NO.: 5);

FIG. 8B shows the nucleic acid sequence of mutant 1: pmimGFP1 with K5E amino acid change (SEQ. ID NO.: 6);

FIG. 9A shows the amino acid sequence of mutant 3: pmimGFP1 with K5T, C8S, and R9A amino acid changes (SEQ. ID NO.: 7); and FIG. 9B shows the nucleic acid sequence of mutant 3: pmimGFP1 with K5T, C8S, and R9A amino acid changes (SEQ. ID NO.: 8).

DESCRIPTION OF THE INVENTION

Figures 1A, 1B:
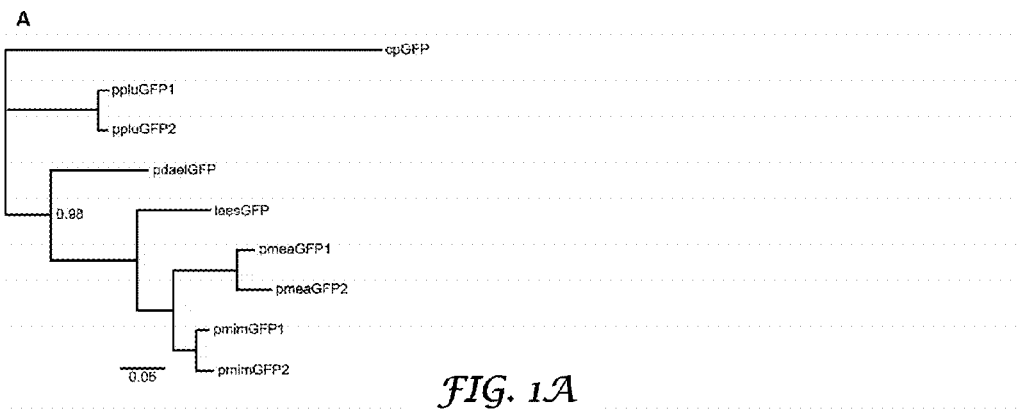
FIG. 1A depicts a phylogeny of the protein-coding sequences of all known copepod GFPs rooted with *Chiridius poppei* GFP (cpGFP), a copepod GFP from the related family Aetideidae. Scale bar: 0.05 substitutions per nucleotide site. The posterior probability at each node is 1.00 except where indicated.
FIG. 1B shows the amino acid sequence alignment of selected copepod GFP proteins and *Aquorea victoria* GFP SEQ. ID NO.: 13. Chromophore-forming tripeptide is underlined. Both the tree and alignment were made using Geneious 3.8 software (12-14). Organisms include *C. poppei* SEQ. ID NO.: 14 (cpGFP, Accession No. AB185173), *L. aestiva* SEQ. ID NO.: 15 (laesGFP, No. AY268073), unidentified *Pontella* SEQ. ID NO.: 16 (pdae1GFP, AY268076), *P. meadi* SEQ. ID NO.: 17 and SEQ. ID NO.: 18 (pmeaGFP1 and GFP2, Nos. AY268074 and AY268075), and *P. plumata* SEQ. ID NO.: 19 and SEQ. ID NO.: 20 (ppluGFP1 and GFP2, Nos. AY268071 and AY268072), and *Pontella mimocerami* SEQ. ID NO.: 1 and SEQ. ID NO.: 3 (pmimGFP1 and GFP2)

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, "nucleic acid" or "nucleic acid molecule" refers to polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., α-enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as azasugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid molecule" also includes so-called "peptide nucleic acids," which comprise naturally-occurring or modified nucleic acid bases attached to a polyamide backbone. Nucleic acids can be either single stranded or double stranded.

An "isolated nucleic acid molecule" as used herein is a nucleic acid molecule that is not integrated in the genomic DNA of an organism. For example, a DNA molecule that encodes a growth factor that has been separated from the genomic DNA of a cell is an isolated DNA molecule. Another example of an isolated nucleic acid molecule is a chemically-synthesized nucleic acid molecule that is not integrated in the genome of an organism. A nucleic acid molecule that has been isolated from a particular species is smaller than the complete DNA molecule of a chromosome from that species.

As used herein the terms "protein", "polypeptide" or "peptide" refer to compounds comprising amino acids joined via peptide bonds and are used interchangeably. A "polypeptide" is a polymer of amino acid residues joined by peptide bonds, whether produced naturally or synthetically. Polypeptides of less than about 10 amino acid residues are commonly referred to as "peptides." A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

An "isolated polypeptide or protein" is a polypeptide or protein that is essentially free from contaminating cellular components, such as carbohydrate, lipid, or other proteinaceous impurities associated with the polypeptide in nature. Typically, a preparation of isolated polypeptide contains the polypeptide in a highly purified form, i.e., at least about 80% pure, at least about 90% pure, at least about 95% pure, greater than 95% pure, or greater than 99% pure. One way to show that a particular protein preparation contains an isolated polypeptide is by the appearance of a single band following sodium dodecyl sulfate (SDS)-polyacrylamide gel electrophoresis of the protein preparation and Coomassie Brilliant Blue staining of the gel. However, the term "isolated" does not exclude the presence of the same polypeptide in alternative physical forms, such as dimers or alternatively glycosylated or derivatized forms.

The term "homology" as used herein refers to the extent to which two nucleic acids are complementary. There may be partial or complete homology. A partially complementary sequence is one that at least partially inhibits a completely complementary sequence from hybridizing to a target nucleic acid and is referred to using the functional term "substantially homologous." The degree or extent of hybridization may be examined using a hybridization or other assay (such as a competitive PCR assay) and is meant, as will be known to those of skill in the art, to include specific interaction even at low stringency As used herein the term "gene" is used to refer to a functional protein, polypeptide or peptide-encoding unit. As will be understood by those in the art, this functional term includes both genomic sequences, cDNA sequences, or fragments or combinations thereof, as well as gene products, including those that may have been altered by the hand of man. Purified genes, nucleic acids, protein and the like are used to refer to these entities when identified and separated from at least one contaminating nucleic acid or protein with which it is ordinarily associated.

As used herein, the term "vector" is used in reference to nucleic acid molecules that transfer DNA segment(s) from one cell to another. The vector may be further defined as one designed to propagate specific sequences, or as an expression vector that includes a promoter operatively linked to the specific sequence, or one designed to cause such a promoter to be introduced. The vector may exist in a state independent of the host cell chromosome, or may be integrated into the host cell chromosome As used herein an "expression vector" is a nucleic acid molecule encoding a gene that is expressed in a host cell. Typically, an expression vector comprises a transcription promoter, a gene, and a transcription terminator. Gene expression is usually placed under the control of a promoter, and such a gene is said to be "operably linked to" the promoter. Similarly, a regulatory element and a core promoter are operably linked if the regulatory element modulates the activity of the core promoter.

As used herein the term "host cell" refers to cells that have been engineered to contain nucleic acid segments or altered segments, whether archeal, prokaryotic, or eukaryotic. Thus, engineered, or recombinant cells, are distinguishable from naturally occurring cells that do not contain recombinantly introduced genes through the hand of man.

The term "sequences" as used herein is used to refer to nucleotides or amino acids, whether natural or artificial, e.g., modified nucleic acids or amino acids. When describing "transcribed nucleic acids" those sequence regions located adjacent to the coding region on both the 5', and 3', ends such that the deoxyribonucleotide sequence corresponds to the length of the full-length mRNA for the protein as included. The term "gene" encompasses both cDNA and genomic forms of a gene. A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA I wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other The terms "a sequence essentially as set forth in SEQ ID NO. (#)", "a sequence similar to" "a sequence identical to", "nucleotide sequence" and similar terms, with respect to nucleotides, refers to sequences that substantially correspond to any portion of the sequence identified herein as SEQ ID NOs.: 1-12. These terms refer to synthetic as well as naturally-derived molecules and include sequences that possess biologically, immunologically, experimentally, or otherwise functionally equivalent activity.

As used herein, the term "polymerase chain reaction" (PCR) refers to the method of K. B. Mullis U.S. Pat. Nos. 4,683,195, 4,683,202, and 4,965,188, hereby incorporated by reference, which describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified". With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as DCTP or DATP, into the amplified segment). In addition to genomic DNA, any oligonucleotide sequence can be amplified with the appropriate set of primer molecules. In particular the amplified segments created by the PCR process itself are, themselves, efficient templates for subsequent PCR amplifications.

The present invention describes the isolation and characterization of two protein isoforms collected green fluorescent copepods. The cDNA expression libraries synthesized from the isolated mRNA yielded the genes responsible for the green fluorescence in the Pontellid copepods and indicated similarities to the GFP first isolated from the jellyfish *Aequorea victoria*.

The two isolated *Pontella mimocerami* GFP-like isoforms are 72% similar to the other known copepod GFP-like proteins, but are much more similar to other Pontellid GFP-like proteins than to the distantly related fluorescent copepod *Chiridius poppei* (family Aetideidae). The new isoforms are quick to mature, rapidly producing a fluorescent signal. The two isoforms are very similar in molar extinction coefficients (ME) with 105,000 $M^{-1}cm^{-1}$ for pmimGFP1 and 103,000 $M^{-1}cm^{-1}$ for pmimGFP2. Quantum yields of pmimGFP1 and pmimGFP2 are 0.94 and 0.92, respectively. The relative brightness of these two new copepod GFP-like proteins is the highest measured for any isolated GFP-like protein.

Fluorescent proteins (FPs) have revolutionized biomedical research. Because of their ability to self-assemble and their non-invasive, non-cytotoxic qualities, fluorescent proteins have been adapted for myriad uses in the labGFP and its derivatives have accelerated life science research by being extensively used as genetically encoded in situ and in vivo markers[38-42] since first being isolated from the jellyfish *Aequorea victoria*, phylum Cnidaria[4-6] To date, about 120 fluorescent and colored GFP-like proteins had been cloned only from hydrozoans and anthozoans of the phylum Cnidaria. Past rationale suggested that fluorescent proteins would be exclusively found in cnidarians and that these proteins would also necessarily be coupled to the luminescent systems that are common in these marine animals.[7-8] However, this dogma was rejected with the discovery that GFP-like proteins could be isolated from other non-luminescent organisms such as corals (Phylum Cnidaria, class Anthozoa), copepods (phylum Arthropoda, class Crustacea), and amphioxus (phylum Chordata, subphylum Cephalochordata).[7,9-10]

So far only seven GFP-like proteins have been identified from the copepod families Pontellidae and Aetideidae.[7,11] In general, the GFP-like proteins from this group of arthropods have qualities such as rapid maturation, high brightness, and increased photostability, all extremely valuable for use as a biotechnology tool. Isolation and characterization of more GFP-like proteins in Pontellidae will likely continue to provide a better source from which to harvest fluorescent proteins that may be adapted for use in the laboratory and in biomedical research.

In the present invention, the inventors cloned, and characterized two novel genes coding for GFP-like proteins from a Pontellid copepod (*Pontella mimocerami*, first described by Fleminger, 1957)[12] in the Atlantic Ocean off the coast of the Bahamas Islands along with the isolation and characterization of two novel GFP-like protein isoforms, pmimGFP1 and pmimGFP2. The two isoforms are similar in their amino acid sequences (FIGS. 6A and 7A, respectively) and share similar spectral characteristics to each other as well as to other copepod GFP-like proteins. The nucleic acid sequences of pmimGFP1 and pmimGFP2, are shown in FIGS. 6B and 7B, respectively. However, the two isoforms of the present invention are the brightest isolated green fluorescent proteins to date.

Figures 4A, 4B:
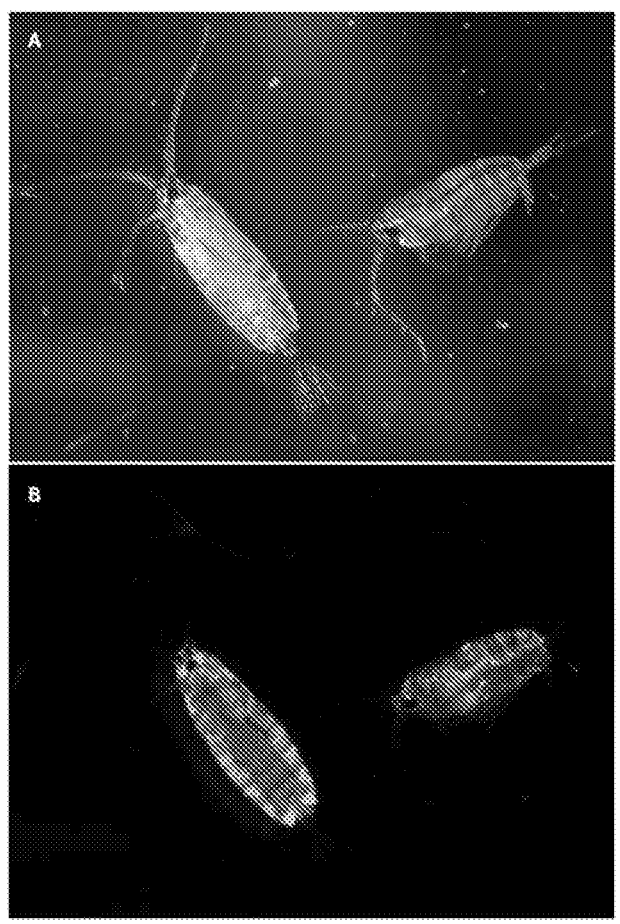
FIGS. 4A and 4B are photographic images showing *Pontella mimocerami* illuminated and imaged under white (4A) and blue light showing the bright green fluorescence (4B). Note the blue non-fluorescent coloration (FIG. 4A) is typical of many Pontellid species.

*Pontella mimocerami* collection and total RNA isolation: The copepods were collected during a sunset plankton tow off the stern of the RV Seward Johnson during the 2007 Deep Scope Cruise. The samples were collected at 25°1.3'N, 77°36.2'W by towing a 200 m plankton net at 5-15 ft below the surface at 1 knot for 20 minutes. After 20 minutes, the net was removed and the collected organisms were inspected with blue light illumination (BlueStar, NightSea; Andover Mass.) to excite the fluorescent proteins. The organisms were photographed under white and blue light provided by a Leica light source and filter (Canon Powershot G6, Leica MZFLIII microscope, and Chroma filter #11003 BL/VIO, FIG. 4). Several green fluorescent copepods were transferred to an empty culture dish with a transfer pipette and identified to the family level, Pontellidae. Total RNA was extracted using a commercial kit (Ambion's RNAqueous kit) according to manufacturer's protocol and the samples were stored on board the ship in 6.65 M LiCl at −80° C. The specimens for identification were preserved by freezing in Tissue-Tek O.C.T. compound and stored at −80° C. (Sakura Finetek; Torrance, Calif.).

Preparation and screening of bacterial cDNA expression library: cDNA was synthesized and PCR-amplified using SMART cDNA amplification kit (Clontech; Mountain View, Calif.) and SuperScript II reverse transcriptase (Invitrogen; Carlsbad, Calif.), with two modifications. First, a different oligonucleotide was used for priming the reverse transcription reaction: 5'AAGCAGTGGTATCAACGCAGAGTCG-CAGTCGGTAC(T)$_{13}$V (where V stands for a mixture of A, G, and C bases) (SEQ ID NO.:9). For the first step in cDNA amplification, the following long oligonucleotide was used in lieu of the one provided with the SMART cDNA amplification kit: AGT GGA CTA TCC ATG AAC GCA AAG CAG TGG TAT CAA CGC AGA GT 3' (SEQ ID NO.:10). The PCR reactions contained 0.3 μM of primers. The thermocycler profile was: 94° C. for 5 m, 94° C. for 40 s, 68° C. for 4 m, cycle to step two for 26 additional cycles, hold at room temperature. The product from this step was diluted 1:10 and 3 μl of this dilution was used for the second step in cDNA amplification. For this second amplification step, three separate reactions were performed. The first one used the same oligonucleotide as in the first amplification step; the other two reactions used the same oligonucleotide, but extended by either one or two T bases at the 5' terminus. These PCR reactions contained 0.1 μM of primer, the thermocycler profile was 94° C. for 5 m, 94° C. for 40 s, 68° C. for 4 m, cycle to step two for 5 additional cycles, hold at room temperature. Such conditions bias the PCR amplification towards longer products[31], generating a cDNA sample enriched with full coding regions. Also, these additional amplifications ensured that upon ligation into vector, each cDNA species would be represented by inserts fused to the leading lacZ peptide in all three possible reading frames. The products of amplification were purified using QIAquick PCR Purification Kit (Qiagen; Valencia, Calif.) and ligated into pGEM-T vector (Promega; Madison, Wis.) following manufacturers' protocols. The ligations were transformed into TOP 10 chemically competent *Escherichia coli* cells (Stratagene; Cedar Creek, Tex.) and the total transformation expression library was plated onto Luria Burtani (LB)/Agar plates supplemented with 100 μg/ml ampicillin and 1 mM Isopropyl β-D-1-thiogalactopyranoside (IPTG). The plates were incubated overnight at 37° C. and then screened at one day post-transformation for green fluorescent colonies using a Leica MZ FLIII microscope with GFP specific filter #51004v2 F/R (Chroma Technology Corp). A total of about 10$^5$ bacterial colonies were surveyed.

Identification, expression, and purification of *Pontella mimocerami* GFP isoforms: GFP1 (SEQ ID NOS.: 1 and 2, amino acid and nucleic acid respectively) and GFP2 (SEQ ID NOS.: 3 and 4, amino acid and nucleic acid respectively):

From the expression plates, six green fluorescent colonies were identified and, were further picked into individual 3 ml LB/Amp (100 μg/ml final concentration) bacterial cultures and shaken overnight at 37° C. The cultures were processed using Qiagen's Spin Mini-Prep kit (Qiagen) following the manufacturer's protocol. 500 ng of each of the six plasmids were sequenced using an ABI 3730 sequencer (Applied Biosystems). The sequences were aligned using SeqMan2 software (DNASTAR Lasergene 7.2) and gene identity was confirmed by BLASTX[32] searching non-redundant protein databases. The amino acid sequences were used to construct a phylogenetic tree using neighbor joining and displaying substitutions per site as well as an alignment of the pmimG-FPs and other copepod proteins with Genious software.[13]

From the amino acid sequences two GFP-like isoforms were identified (SEQ ID NOS.: 1 and 3). Two plasmid constructs, pmimGFP1 and pmimGFP2, were chosen representing both isoforms to use as templates to re-amplify the gene coding regions with an N-terminus Shine-Dalgarno sequence, 5' TTG ATT GAT TGA AGG AGA AAT ATC ATG (SEQ ID NO.:11) and a C-terminus 6-histidine tag, 5' CAT CAC CAT CAC CAT CAC TAA A (SEQ ID NO.:12).[14-15] The primers were designed to be in frame with the gene specific primer for each isoform. The resulting amplicons were ligated into the same pGEM-T vector from Promega, but then transformed into protein expression specific Z cells (Zymo Research, Orange, Calif.). The transformations were plated onto LB/Agar plates supplemented with 1×Amp and 1×IPTG (concentrations as previously noted), and incubated overnight at 37° C. One green fluorescent colony was picked from each plate, resuspended in 20 μL of water, and streaked onto fresh LB/Agar plates supplemented with 1×Amp and 1×IPTG (concentrations as previously noted), and incubated overnight at 37° C. One green fluorescent colony was picked from each plate, suspended in 20 μL of water, and streaked onto fresh LB/Agar plates supplemented with 100 μg/ml ampicillin and 1 mM IPTG. After a two-day incubation at room temperature, the colonies were harvested from plates and suspended in 1×PBS, sonicated on ice, and centrifuged to remove the cellular debris. The inventors used the cleared lysate to isolate a purified solution of the green fluorescent protein using metal-affinity chromatography as implemented in QIAexpressionist system following the manufacturer's protocol (Qiagen). The fluorescent proteins were eluted in 500 mM imidazole in 1×PBS. The imidazole was removed by buffer exchange for 1×PBS by repeated centrifugation steps in a protein concentrator (Amicon Ultra—15, Millipore; Billerica, Mass.).

Phylogenetic analysis: A nucleotide alignment of all copepod GFP-like proteins was prepared with Geneious software v 3.7.[16] The Bayesian phylogenetic analysis was performed on the basis of coding nucleotide sequence alignment, using MrBayes software embedded within Geneious package.[13,16] The Bayesian analysis was performed using a generalized time reversible model of the alignment was done to reveal the phylogenetic tree, rooted to the closely related *Chiridius poppei*.[17-18] An amino acid sequence alignment, including *A. victoria* GFP was prepared with Geneious software, v 3.8.[16] The trees were sampled every 200 steps generating 5,500 trees, of which the first 5,000 were discarded ("burned"), and the remaining 500 trees were used to infer posterior probabilities. The tree was rooted by the closely related cpGFP from *Chiridius poppei*, which comes from another family of calanoid copepods (Aeteidae, 13). An amino acid sequence alignment, including *A. victoria* GFP, was prepared with Geneious software.[13] The analyzed sequences included GFPs from *Chiridius poppei* (cpGFP, Accession No. AB185173), Labidocera aestiva (laesGFP, No. AY268073), unidentified Pontella (pdae1GFP, AY268076), Pontella meadi (pmeaGFP1 and GFP2, Nos. AY268074 and AY268075), and Pontella plumata (ppluGFP1 and GFP2, Nos. AY268071 and AY268072).

Molar extinction measurements: Determination of the molar extinction coefficient (ME) was based on the fact that the green-emitting GFP chromophore in the alkali-denatured protein has a characteristic peak of absorption at 445 nm with a molar extinction coefficient of 44,000 liter mol$^{-1}$cm$^{-1}$,[33] which is independent of the sequence of the protein since the influence of the sequence-specific chromophore environment is removed by denaturation. This fact provides a useful internal standard for determination of the ME in the native state in any GFP-like protein with a GFP-like chromophore. This strategy was first suggested by Gurskaya et al[34], and since then was adopted in several studies characterizing natural GFP-like proteins[9,35]. The measurement involves determining the absorption of the same concentration of the protein in alkali-denatured and native conditions, and calculating the native ME based on a simple proportion. Strictly speaking, the ME determined in this way correspond to the fully-formed GFP chromophore, not the protein; but since each properly functioning GFP-like polypeptide generates and hosts exactly one chromophore molecule, it is possible view this measurement as absorption of 1M concentration of protein chains under ideal conditions (100% chromophore biosynthesis efficiency and no degradation). This measure is independent of the oligomeric state of the protein, and is free of potential sources of error related to measurements of protein concentration or biases due to incomplete chromophore maturation, therefore providing grounds for comparison of brightness characteristics across GFP-like proteins from various sources. In this study, to achieve better accuracy, the inventors measured the ME using a range of concentrations. Fluorescent proteins (0.8 µg, 2 µg, 4 µg, 6 µg, and 8 µg protein) were diluted in either denaturing (0.1M NaOH) or non-denaturing (1×PBS) buffers, in a total volume of 150 µl. The absorbance was read for all the samples from 400 nm-550 nm with a 5 nm interval. Then, the maximal absorbance values of the native proteins were plotted against the absorbances at 445 nm of the denatured proteins for the range of dilutions. The ME of the native protein was calculated as the slope of the linear regression of this graph multiplied by the ME of the denatured GFP chromophore at 445 nm (44,000 liter mol$^{-1}$cm$^{-1}$,[33]).

Fluorescence quantum yield measurements: To determine the quantum yield of fluorescence (QY, the fraction of photons emitted of the total number of photons absorbed), the same dilutions of the native proteins were excited at 450 nm and the relative fluorescence output between 480 nm and 600 nm was determined by summing up all the fluorescence values for each wavelength with a 5 nm interval. The same set of dilutions for the QY standards (fluorescein, QY=0.9 and EGFP, QY=0.6) were prepared and measured in a similar fashion. The total fluorescence for each dilution was plotted against the absorbance of each dilution at excitation wavelength (450 nm). The QYs of the new proteins of the present invention were calculated by comparing the linear regression slopes of our samples to those of our standards. The error of the QYs measurements was calculated using the Delta method [36]. For all quantitative spectroscopic measurements, SpectraMax M2 microplate reader with the provided software (Molecular Devices, SoftMax Pro v5; Sunnyvale, Calif.) was used.

Oligomerization and aggregation: To determine the oligomeric status of the new copepod GFP-like proteins of the instant invention, the inventors analyzed the proteins using SDS-PAGE in a 4-15% gradient gel with SDS-Tris-Glycine buffers (Bio-Rad, Hercules, Calif.). To resolve GFP-like proteins in the native state, the samples were not boiled before loading on the gel, and visualized after the run by their native fluorescence. This method of oligomerization assessment utilizes the fact that most GFP-like proteins do not lose their oligomeric state or fluorescence unless boiled in SDS, and their mobility on an SDS gel roughly corresponds to their globular size. This was first noticed and exploited in studies of oligomerization of the red fluorescent protein DsRed[18], followed by demonstration of the utility of this approach for assessing oligomerization in a variety of other GFP-like proteins[19,35]. Since it is theoretically possible that SDS would disrupt oligomers but not unfold the protein, the method is applied conservatively, such that the only result that is considered relevant is the presence of oligomerization or aggregation, whereas the apparent lack of oligomerization does not necessarily imply the monomeric state of the protein in the absence of SDS. Since the mobility of such non-denatured protein does not correspond to its molecular weight measured by the markers that assume full polypeptide unfolding, a special set of standards for appropriate globule sizes is necessary to evaluate the oligomeric state. In the present invention, as monomeric and tetrameric standards, the inventors used recombinant GFP (rGFP) and DsRed2 proteins, respectively (Clontech, Mountain View, Calif.). In gels obtained in the present invention, the native monomeric GFP ran as a band at 37 kDa, while tetrameric DsRed2 ran at 60 kDa. The mobility of these standards was consistent across gels, making it possible to use the standard marker lane (BioRad, Hercules, Calif.) to infer their position. In addition to SDS-PAGE of unboiled samples with band visualization via native fluorescence, the inventors also ran the same samples after boiling (i.e., under fully denaturing conditions) on the same gels, and used coomassie staining to identify the bands specific for the unboiled samples.

Site-directed mutagenesis: To reduce aggregation, the present invention describes several amino acid changes in the N-terminal that were introduced into the gene sequence using PCR with primers designed to amplify the gene. Mutant 1 introduced K5E (SEQ ID NOS.:5 and 6, amino acid and nucleic acid respectively) as shown in FIGS. 8A and 8B, respectively, mutant 2 introduced K5T, and mutant 3 introduced K5T, C8S, and R9A changes (SEQ ID NOS.: 7 and 8, amino acid and nucleic acid respectively, as seen in FIGS. 9A and 9B).[19] Additionally, several internal amino acids were changed (139, 192, 221) were changed using Stratagene's Site Directed Mutagenesis Kit. The modifications include mutating the Cys at 139 to Ser and the Phe at 192 and 221 to either Ala or Asp. These three amino acids (Cys and two Phe) were chosen specifically to change the oligomeric status of the native protein from a tetramer to an oligomer.

pH stability: Chromophore sensitivities to changes in pH were assayed for pmimGFP1, pmimGFP2, pmimGFP1 (K5T, C8S, R9A), and EGFP (BioVision, Mountain View, Calif.). Roughly 10 µg of the proteins (5 µg for eGFP) were incubated in buffers of varying pH for 10 min at 25° C., followed by measuring the maximum fluorescence intensity of each. All the proteins were excited at 450 nm and emission was measured from 480 to 600 nm. The buffers included: 0.1M glycine/HCl (pHs 3.0 and 3.5), 0.1M sodium acetate (pHs 4.0, 4.5, and 5.0), 0.1M phosphate (pH 6.0), 0.1M HEPES (pH 7.0), 0.1M Tris/HCl (pHs 8.0 and 9.0), 0.1M carbonate (pHs 10.0 and 11.0), 0.1M phosphate/NaOH (pHs 11.5, 12.0, 12.5, and 13.0) and 0.1M NaOH (pH 13.5). Data were collected and graphed using the same instruments as for QY.

Photostability: 1 μl of protein solutions—EGFP (BioVision, Mountain View, Calif.), pmimGFP1, and pmimGFP1 (K5T, C8S, R9A)—of approximately 1 μg/ml concentration were added to 100 μl of immersion oil (Fluka/Sigma, St. Louis, Mo.), were both vortexed for 5 s to obtain emulsion. To generate negative control droplets, 1 μl of 1×PBS was emulsified in the same way and mixed in equal proportions with the protein emulsions. A droplet of this combined emulsion was placed onto a slide and slip-covered, with 3 replicate slides made for each protein. Individual droplets on the slides were illuminated through a 40× objective (Eclipse E600 microscope, Super High Pressure Mercury Lamp, CFI PLAN APO 40× objective, FITC-HYQ filter, Nikon, Japan) over the course of 10 minutes while collecting images every 30 s (exposure 800 ms, TV Lens C-0.6x, Nikon, OpenLab Software by Improvision, UK). The integrated density (sum of all pixel values) of a non-fluorescent droplet (filled with 1×PBS) was used as a background and subtracted from the density of a corresponding fluorescent droplet (on the same slide), with the help of Image J software (National Institutes of Health, Bethesda, Md.). These values were plotted against time, and half-time of bleaching for the newly cloned proteins was inferred relative to EGFP.

Sequence and phylogenetic analysis: The nucleotide-based phylogenetic tree of the new pmimGFPs in relation to all other copepod fluorescent proteins (FIG. 1A) show support at 1.00 at every node except for where noted (posterior probability of 0.98 between pdae1GFP and the laesGFP/pmea/pmim group). The amino acid sequences (SEQ ID NOS.:1 and 3) of the two isoforms of our copepod GFPs are 97% similar to each other (only 6 amino acids difference) and are presented in alignment to other known copepod GFPs (FIG. 1B). Overall, 37% of the amino acid sequence is identical among all of the copepod GFL-like sequences, and 72% of the sequence was conserved among all of the copepod GFP-like sequences. The sequences are presented as a phylogenetic tree in relation to all other major groups of fluorescent proteins that have been characterized to date (FIG. 1A).[13] The amino acid sequences of the two isoforms of our copepod GFPs are 97% similar to each other (only 6 amino acids difference), and are presented in alignment to other known copepod GFPs using Geneious software (FIG. 1B).[13]

Figure 2:
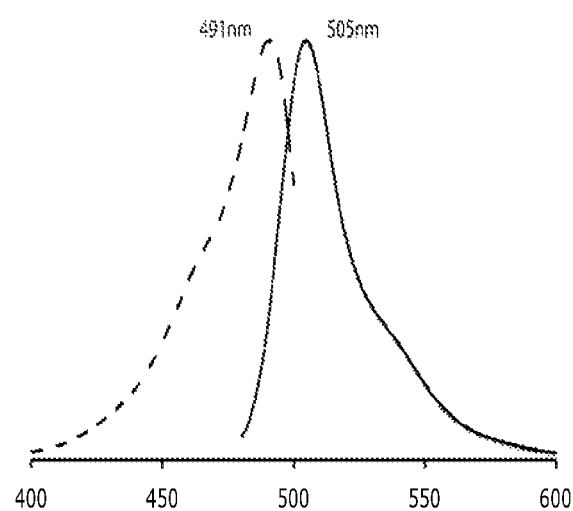
FIG. 2 shows Normalized excitation (dashed line) and emission (solid line) curves of purified pmimGFP1 and pmimGFP2. Horizontal axis: wavelength in nanometers; vertical axis: fluorescence amplitude. Dashed line represents excitation maximum at 491 nm, solid line represents emission maximum at 505 nm for both pmimGFP isoforms.

Molar extinction coefficients and quantum yields of pmimGFP1 and pmimGFP2: Both of the purified *Pontella* GFPs were soluble in PBS with 500 mM imidazole during the final elution step of purification. However, when the imidazole was removed, the proteins formed large aggregates that almost completely precipitated out of solution. In order to perform the spectral and protein gel analyses, 250 mM imidazole was added back to the protein solution, which re-solubilized the aggregates. The spectral analyses revealed that the new copepod GFP-like proteins of the present invention are similar in some aspects to the other Pontellid GFP-like proteins, with the exception of *Chiridius poppei*, a copepod from the Aetideiae family. The molar extinction coefficients for pmimGFP1 and pmimGFP2 are 105,000 $M^{-1}cm^{-1}$ and 103,000 $M^{-1}cm^{-1}$ respectively, notably higher than the average copepod molar extinction coefficient of about 89,000 $M^{-1}cm^{-1}$. Quantum yields of pmimGFP1 and pmimGFP2 are 0.94 and 0.92, respectively, notably exceeding even the highest QY seen in a copepod species (*Pontella meadi* at 0.74). However, the calculated absorption and emission peaks of pmimGFP1 and pmimGFP2 (491 and 505 respectively, FIG. 2) are very similar to the other copepod GFP-like proteins (absorbance max between 480-490 nm, emission max between 500-511 nm).

Figures 3A, 3B:
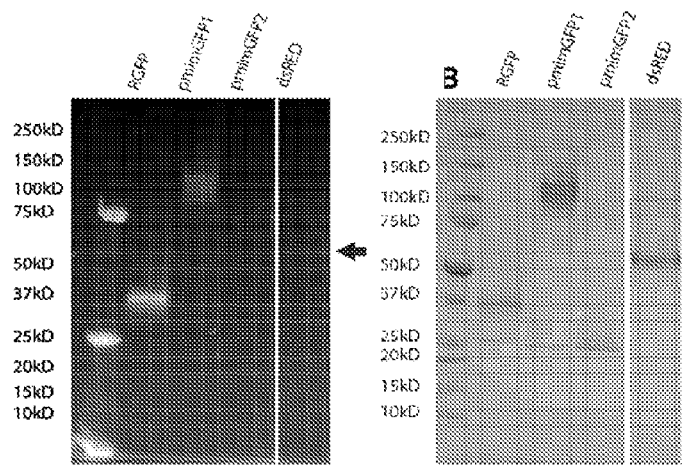
FIG. 3A shows recombinant fluorescent proteins electrophoresed on a SDS-containing gel without prior heating and viewed with UV illumination. pmimGFP1 fluoresces brightly, pmimGFP2 is also visible, but is very faint. rGFP is a monomer, DsRed is a tetramer (indicated by an arrow)
FIG. 3B is the same semi-denatured gel as in FIG. 3A, but imaged with Coomassie stain. rGFP, pmimGFP1, and pmimGFP2 are all susceptible to partial denaturation under the running conditions and therefore show non-fluorescent bands at ~25 kD, the expected size of a fully denatured protein. DsRed, the tetrameric standard, retains its multimeric state.
Figures 3C, 3D:
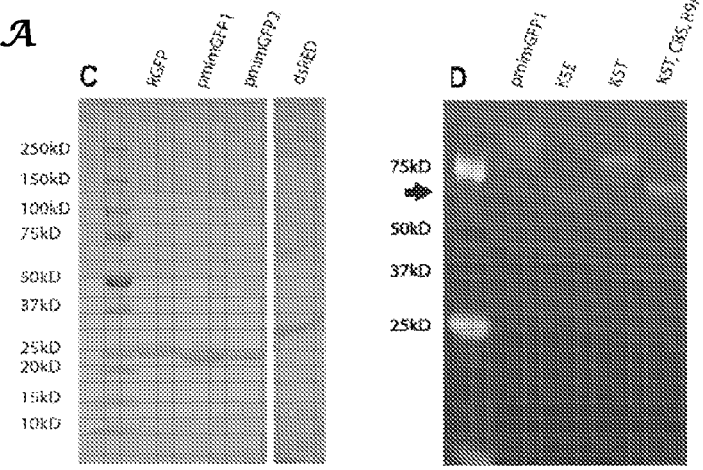
FIG. 3C shows the same samples as in FIGS. 3A and 3B, but electrophoresed in fully denaturing conditions (before loading, the samples were boiled 5 min) followed by Coomassie stain. All four samples show the single major band corresponding to the denatured protein at about 25 kD.
FIG. 3D shows the removal of N-terminal positive charges reduces aggregation. Lane 1 is the wild type pmimGFP1, lane 2 K5E mutant, lane 3 is K5T mutant, and lane 4 is a triple mutant K5T, C8S, and R9A. Arrow indicates tetramer mobility.

SDS-PAGE of unboiled samples of the pmimGFP1 and pmimGFP2 shows native fluorescence as lower mobility bands as compared to the monomeric recombinant GFP (rGFP) and even tetrameric DsRed proteins (FIGS. 3A-3C), which suggests aggregated of high-order oligomeric forms. There seems to be pronounced difference between pmimGFP1 and pmimGFP2 resistance to SDS-induced unfolding. In SDS-PAGE of unboiled samples, pmimGFP1 fluoresces strongly, while pmimGFP2 is barely visible roughly at the tetramer mobility (FIG. 3A). Coomassie staining of the same lanes (FIG. 3B) indicated that the majority of pmimGFP2 protein appears as a band at 25 kDa, corresponding to the mobility of the protein under fully denatured conditions (note that every GFP-like protein in this gel actually unfolds somewhat in SDS even without boiling). FIG. 3C shows all of the proteins in a fully denatured state, with all protein masses around 25 kDa. Both copepod proteins are 222 amino acids long with a predicted molecular weight of 25 kDa.

A previous study demonstrated that, in many GFP-like proteins, the aggregation tendency can be reduced by replacing a few positively charged amino acids in the N-terminus by neutral or negatively charged ones[19]. The present inventors chose to replace three amino acids, two positively charged ones (K5 and R9), and one cysteine (C8) as a potential disulphide bridge-forming one. FIG. 3D shows an SDS-PAGE of unboiled samples of mutants of pmimGFP1. Mutant 1 (K5E) shows increased mobility (i.e., less aggregation/oligomerization), but also substantially decreased brightness. Mutant 2 (K5T) is still very bright, but shows no change in mobility. Mutant 3 (K5T, C8S, R9A) matches the mobility of the tetrameric standard (DsRed2) and appears bright in the gel. From the above findings, it can be concluded that, although the mutagenesis alleviates aggregation, the best mutant protein of the present invention still forms oligomers, most likely tetramers. Despite its apparent brightness, the triple mutant also demonstrates diminished molar extinction coefficient (75,000 $M^{-1}cm^{-1}$) and quantum yield (0.35) in comparison to the parent protein, indicating that either the breakdown of the higher-order aggregates, or the effect of the particular mutations within a single monomer, were detrimental for the protein's brightness characteristics.

Figure 5A:
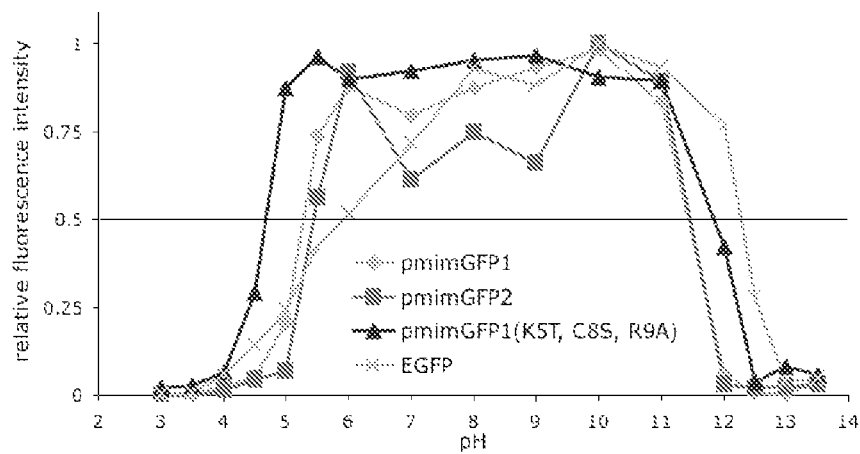
FIGS. 5A and 5B show pH (5A) and photo (5B) stability of novel copepod proteins and of the non-aggregating mutant of pmimGFP1. On both panels, analogous measurements of commercially available recombinant EGFP protein are presented as a reference.
Figure 5B:
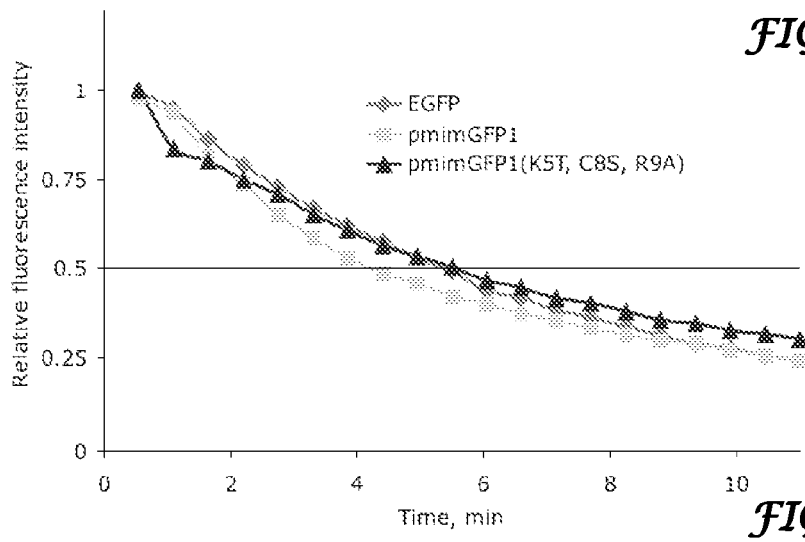

The new proteins are more stable in acidic pH than EGFP, demonstrating a pKa around 5.3-5.4, with the non-aggregating mutant of pmimGFP1 (K5T, CBS, R9A) being the most stable across the whole pH range, with the pKa of 4.7 (FIG. 5A) pmimGFP2 also exhibits a tendency to be less bright in the neutral pH range, which, however, is not always reproducible and may depend on other factors such as protein concentration and temperature fluctuations. The photostability was assayed for the pmimGFP1 and its non-aggregating mutant relative to EGFP in the conditions approximating a typical application of the protein as a genetically encoded fluorescent label, by comparing the rates of photobleaching of protein emulsion droplets under the fluorescent microscope (FIG. 5B). The time to half-photobleaching of pmimGFP1 is 0.8 of EGFP, while its non-aggregating mutant is essentially identical to EGFP in this regard. Both pmimGFP1 and its mutant show non-exponential dynamics of photobleaching, with the highest photobleaching rate at the start of exposure. Notably, past the half-bleaching point both proteins photobleach at a similar rate, which is slightly lower than for EGFP (FIG. 5B).

Copepod luminescence was first documented long ago, but it was also observed that some luminescent species exhibited an additional fluorescence located at the site of the luminous glands.[20, 21] However, the genus of copepods that were collected in the present invention, *Pontella*, exhibited only green fluorescence and no luminescence.[21] Since these organisms are not luminescent, it eliminated the need for the fluorescent protein serving as a chromatic shift agent, hinting that green fluorescence in these creatures can serve some other function. Although copepods don't feature compound eyes such as some other crustaceans, the *Pontellidae nauplius* eye is well developed, featuring an elaborate triple-lens construction in the enlarged ventral eyes in the males[22] and even though the biological roles for Pontellidae fluorescence are not proven, having well developed eyes in males may assist in locating brightly fluorescent females and interspecies signaling. Pontellidae fluorescence may also offer protective counter-shading, i.e., protecting the copepods from recognition in their oceanic environment[9, 23-24] this function would be analogous to the well-documented function of bioluminescence in dim ocean zones.[9,23,24,37]

Sequence analysis revealed that pmimGFP1 and pmimGFP2 proteins had their N-terminal methionines intact, which was not the case with the *Chiridius poppei* GFP-like protein.[11] Masuda suggested that this may be due to post-translational excision of the methionine by bacterial methionyl-aminopeptidase (MAP). The second amino acid in the *C. poppei* GFP-like protein is threonine, which is known to leave the primary methionine vulnerable to removal. All of the Pontellid GFP-like proteins have a proline in the second position, which may be protective.[25-27] These similarities contribute support for the closer phylogenetic relationships among the Pontellid GFP-like proteins. FIG. 1A represents the phylogenetic tree of all of the known copepod GFP-like proteins. The tree suggests that *C. poppei* is at least closely related to the other Pontellid copepod species, expected since *C. poppei* belongs to a different copepod family, Aetideidae. The light transforming chromophores of both pmimGFP1 and pmimGFP2 proteins contain the same amino acid sequence, Gly-Tyr-Gly, as the other known copepod GFP-like proteins; the Tyr and second Gly are strictly conserved among all fluorescent proteins. Also, the Arg and Glu amino acids responsible for the autocatalytic steps of chromophore formation are present at positions 96 and 222, respectively GFP numbering (positions 87 and 221 in the pmimGFPs). Copepod GFP-like sequences tend to lack tryptophan residues[9]; pmimGFP1 and pmimGFP2 each have only one at position 158. The only other copepod GFP-like protein to contain tryptophan is from *L. aestiva*, which may share a common ancestor with the two new copepod fluorescent isoforms.

The molar extinction and quantum yield data reveal that the new *Pontella* GFP-like proteins of the present invention are the brightest green fluorescent proteins to be isolated in their native forms with a relative brightness of 120 $M^{-1}cm^{-1}$ (product of the molar extinction coefficient and the quantum yield). Only one other fluorescent protein, a derived form of dsRed called tdTomato approaches the brightness of the pmimGFPs with a relative brightness of 95 $M^{-1}cm^{-1}$.[28] Both pmimGFP1 and pmimGFP2 isoforms are almost three times brighter than the *P. plumata* GFP-like proteins, more than 1.5 times brighter than all of the other copepod GFP-like proteins, and more than five times brighter than the cardinal GFP from *A. victoria*. Thus, these new pmim copepod GFP-like proteins make excellent reporter proteins.[29]

Although the first GFP-like proteins from copepods were suggested to be monomeric, it has since been established that some were tetramers.[9,21] The data from the present invention suggests that pmimGFP1 exists in a multimeric form of at least a tetramer (FIGS. 3A to 3C), not unusual for fluorescent proteins PmimGFP2, despite very high sequence similarity to pmimGFP1, seems to be much more sensitive to the presence of SDS: it almost completely unfolds even when the sample is not heated, with the remaining native protein running as a very faint band roughly corresponding to the tetrameric size (FIGS. 3A-3C). The only protein in the gel that is monomeric is rGFP; dsRED, a red fluorescent protein, is a tetramer.

Both pmimGFP1 and pmimGFP2 aggregate and almost completely precipitate out of solution. Evdokimov noted a similar tendency to aggregate in the copepod GFP-like protein, ppluGFP2[9], and suggested this aggregation may be the result of electrostatic interactions between the charged surfaces of the fluorescent protein.[21,30] Evdokimov's research used a site-directed mutagenesis approach to develop a non-aggregating version of ppluGFP2 protein, now designated as TurboGFP. In the present invention several amino acid residues (K5, C8, and R9) at the N-terminus were replaced with others (E, T, S, or A) that are less likely to enhance aggregation[19] as well as to remove the 6xHis tag. Mutant 3 of the present invention, containing all three amino acid changes and the removed his tag, was the most successful mutant since it does not show aggregation beyond the tetrameric level and appears bright on the gel, although its quantum yield (0.35) becomes substantially less than in the parental protein.

The brightness of a GFP-like protein is proportional to the product of two factors: molar extinction coefficient (ME) and quantum yield (QY). Of these, ME strongly depends on the excitation wavelength, in the fashion described by the absorption spectrum of the protein. With a particular application in mind, it may be useful to compare the brightness characteristics of all proteins at a fixed excitation wavelength dictated by the application, which is sometimes done by companies advertising their GFP-related markers. In most cases, however, to compare general photophysical properties of GFP-like proteins their brightness is defined as a product of QY and ME at the own absorption maximum of each protein, for which the standard reported ME corresponds. This "calculated brightness" is different from the absolute brightness, which is defined as the number of photons emitted divided by the number of photons incident on the chromophore, but is assumed to be directly proportional to it and hence represents a useful measure for comparison. In terms of calculated brightness, the new *Pontella mimocerami* proteins described herein are the brightest green emitting fluorescent proteins known to date, with a calculated brightness of 95,000-99,000 $M^{-1}cm^{-1}$. Only one other fluorescent protein, a red protein derived from DsRed called tdTomato, approaches this value with a calculated brightness of 95,000 $M^{-1}cm^{-1}$ (35). The calculated brightness of the new proteins is three-fold greater than the one of EGFP, the most widely used genetically encoded fluorescent marker. Thus, these new copepod GFP-like proteins have a good potential to become excellent reporters, at least in applications that tolerate oligomeric FP labels (such as monitoring promoter activity, organelle tracking, or cell and tissue labeling). Still, their very high aggregation tendency would be a problem even for such applications, which prompted the present inventors to create a mutant of pmimGFP1 that does not aggregate (although still oligomerizes). Interestingly, the non-aggregating mutant demonstrates a higher pH stability (pKa=4.7) than its ancestral pmimGFP1, but has a calculated brightness of only 26,000 $M^{-1}cm^{-1}$. Additional random mutagenesis may help to restore some of the lost brightness. Further mutagenesis is also required for adaptation of the new proteins for imaging applications involving molecular fusions, which must rely on monomeric protein tags.

The present invention describes two novel FPs from *Pontella mimocerami* (Copepoda, Calanoida, Pontellidae), collected off the coast of the Bahamas Islands. These two proteins, pmimGFP1 and pmimGFP2, were identified via fluorescence screening bacterial cDNA expression library prepared from whole-body RNA of *P. mimocerami*. The FPs described hereinabove, have high molar extinction coefficients (105,000 $M^{-1}cm^{-1}$ for pmimGFP1 and 103,000 $M^{-1}cm^{-1}$ for pmimGFP2), as well as high quantum yields (0.94 for pmimGFP1 and 0.92 for pmimGFP2). The spectroscopic characteristics of the two FPs from *P. mimocerami* make them the brightest green FPs ever described in the literature, whether isolated from a natural source or engineered in the laboratory. Because of this, these proteins are a valuable addition to any in vivo imaging toolkit.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

[1] WO/1995/007643: Uses of Green Fluorescent Protein.

[2] U.S. Pat. No. 5,625,048: Modified Green Fluorescent Proteins.

[3] US Patent Publication No. 20040086968: Mutants of green fluorescent protein.

[4] Lippincott-Schwartz, J., and G. H. Patterson. 2003. Development and use of fluorescent protein markers in living cells. Science 300:87-91.

[5] Chudakov, D. M., S. Lukyanov, and K. A. Lukyanov. 2005. Fluorescent proteins as a toolkit for in vivo imaging. TRENDS in Biotechnology 23:605-613.

[6] Shimomura, O., F. H. Johnson, and Y. Saiga. 1962. Extraction, purification, and properties of Aequorin, a bioluminescen protein from luminous Hydromedusan, *Aequorea*. J. Cell Comp. Physiol. 59:223-239.

[7] Matz, M. V., A. F. Fradkov, Y. A. Labas, A. P. Savitsky, A. G. Zaraisky, M. L. Markelov, and S. A. Lukyanov. 1999. Fluorescent proteins from nonbioluminescent species. Nat. Biotechnol. 17:969-973.

[8] Matz, M. V., K. A. Lukyanov, and S. A. Lukyanov. 2002. Family of the green fluorescent protein: journey to the end of the rainbow. BioEssays 24:953-959.

[9] Shagin, D. A., E. V. Yanushevich, A. F. Fradkov, K. A. Lukyanov, Y. A. Labas, T. N. Semenova, J. A. Ugalde, A. Meyers, J. N. Nunez, E. A. Widder, S. A. Lukyanov, and M. V. Matz. 2004. GFP-like proteins as ubiquitous metazoan superfamily: evolution of functional features and structural complexity. Mol. Biol. Evol. 21:841-850.

[10] Deheyn, D. D., K. Kubokawa, J. K. McCarthy, A. Murakami, M. Porrachia, G. W. Rouse, and N. D. Holland. 2007. Endogenous green fluorescent protein (GFP) in amphioxus. Biol. Bull. 213:95-100.

[11] Masuda, H., Y. Takenaka, A. Yamaguchi, S, Nishikawa, H. Mizuno. 2006. A novel yellowish-green fluorescent protein from the marine copepod *Chiridius poppei*, and its use as a reporter protein in HeLa cells. Gene 372:18-25.

[12] Fleminger, A. 1957. New Calanoid copepods of *Pontella* Dana and *Labidocera* Lubbock with notes on the distribution of the genera in the Gulf of Mexico. Tulane Stud. Zool. 5:19-34.

[13] Drummond A J, Ashton B, Cheung M, Heled J, Kearse M, Moir R, Stones-Havas S, Thierer T, Wilson A (2007) Geneious v3.8, Available from http://www.geneious.com/

[14] Shine, J. and Dalgarno, L. 1975. Determinant of cistron specificity in bacterial ribosomes. Nature 254 (5495): 34-8.

[15] Hochuli, E. 1988. Large-scale chromatography of recombinant proteins. J Chromatogr. July 1; 444:293-302.

[16] Huelsnebeck, J. P. and F. Ronquist, 2001. MRBAYES: Bayesian inference of phylogenetic trees. Bioinformatics 17:754-755.

17. Tavare, S. 1986. Some probablilistic and statistical problems in the analysis of DNA sequences. American Mathematical Society: Lectures on Mathematics in the Life Sciences. 17:57-86.
18. Baird, G. S., D. Z. Zacharias, R. Y. Tsien. 2000. Biochemistry, mutagenesis, and oligomerization of DsRed, a red fluorescent protein from coral. PNAS. 97(22):11984-11989.
19. Yanushevich, Y. G., D. B. Staroverov, A. P. Savitsky, A. F. Fradkov, N. G. Gurskaya, M. E. Bulina, K. A. Lukyanov, S. A. Lukyanov. 2002. A strategy for the generation of non-aggregating mutants of Anthozoa fluorescent proteins. FEBS Letters 511:11-14.
20. Harvey, E. N., 1952. Bioluminescence. Academic Press, N.Y., 649 pp.
21. Herring, P. J. 1988. Copepod luminescence. Hydrobiologia 167/168:183-195.
22. Land, M., F. 1988. The functions of eye and body movements in Labidocera and other copepods. J. exp. Biol. 140:381-391.
23. Ohtsuka, S., R. Huys. 2001. Sexual dimorphism in calanoid copepods: morphology and function. Hydrobiologia 453/454:441-466.
24. Evdokimov, A. G., M. E. Pokross, N. S. Egorov, A. G. Zaraisky, I. V. Yampolsky, E. M. Merzlyak, A. N. Shkorporov, I. Sander, K. A. Lukyanov, and D. M. Chudakov. 2006. EMBO 7:1006-1012.
25. Hirel, H., J. Schmitter, P. Dessen, G. Fayat, and S. Blanquet. 1989. Extent of N-terminal methionine excision from Escherichia coli proteins is governed by the side-chain length of the penultimate amino acid. PNAS 86:8247-8251.
26. Tobias, J. W., T. E. Shrader, G. Rocap, and A. Varshaysky. 1991. The N-end rule in bacteria. Science 254(5036): 1374-1377.
27. Mogk, A., R. Schmidt, and B. Bukau. 2007. The N-end rule pathway for regulated proteolysis: prokaryotic and eukaryotic strategies. TRENDS in Cell Biology 17(4):165-172.
28. Shaner N. C., R. E. Campbell, P. A. Steinbach, B. N. G. Giepmans, A. E. Palmer, and R. Y. Tsien. 2004. Improved monomeric red, orange and yellow fluorescent proteins derived from Discosoma sp. red fluorescent protein. Nature Biotechnology 22(12):1567-1572.
29. Shaner, N. C., G. H. Patterson, and M. W. Davidson. 2007. Advances in fluorescent protein technology. Journal of Cell Science 120(24):4247-4260.
30. Himanen, J. P., Popowicz, A. M., and J. M. Manning. 1997. Recombinant sickle hemoglobin containing a lysine substitution at Asp-85(a): expression in yeast, functional properties, and participation in gel formation. Blood 89:4196-4203.
31. Shagin, D. A., K. A. Lukyanov, L. L. Vagner, and M. V. Matz. 1999. Regulation of average length of complex PCR product. Nucleic Acids Research. 27(18):e23.
32. Altchul, S. F., W. Gish, W. Miller, E. W. Myers, and D. J. Lipman. 1990. Basic local alignment search tool. J. Mol. Biol. 215:403-410.
33. Ward, W. W. 1981. Properties of the coelenterate green-fluorescent proteins. Bioluminescence and Chemiluminescence: Basic Chemistry and Analytical Applications. DeLuca, M., and McElroy, D. W., Eds. New York, N.Y.: Academic Press, pp. 235-242.
34. Gurskaya, N. G., A. F. Fradkov, N. I. Pounkova, D. B. Staroverov, M. E. Bulina, Y. G. Yanushevich, Y. A. Labas, S. Lukyanov, and K. A. Lukyanov. 2003. Colourless green fluorescent protein homologue from the non-fluorescent hydromedusa Aquorea coerulescens and its fluorescent mutants. Biochem. J. 373:403-408.
35. Alieva, N. O., Konzen, K. A., Field, S. F., Meleshkevitch, E. A., Hunt, M., Beltran-Ramirez, V., Miller, D. J., Wiedenmann, J., Salih, A. and Matz, M. V. 2008. Diversity and evolution of coral fluorescent proteins. PLoS ONE 3(7): e2680.
36. Miller, J. C, and J. N. Miller. 1988. Basic statistical methods for analytical chemistry part I: Statistics of repeated measurements, A review. Analyst, September, Vol. 113.
37. Matz, M. V., Y. A. Labas, and J. Ugalde. 2006. Evolution and function of color in GFP-like proteins. Green fluorescent protein: Properties, applications, and protocols, second edition (Chalfie, M. and S. R. Kain eds). Wiley Interscience. 47:139-161.
38. Chalfie, M., Y. Tu, G. Euskirchen, and W. W. Ward. 1994. Green fluorescent protein as a marker for gene expression. Science 263:802-805.
39. Amsterdam, A., S. Lin, and N. Hopkins. 1995. The Aequorea victoria green fluorescent protein can be used as a reporter in live zebrafish embryos. Dev. Biol. 171:123-129.
40. Sheen, J., S. Hwang, Y. Niwa, H. Kobayashi, and D. W. Galbraith. 1995. Green-fluorescent protein as a new vital marker in plant cells. The Plant Journal 8(5):777-784.
41. Ikawa, M., K. Kominami, Y. Yoshimura, K. Tanaka, Y. Nishimune, and M. Okabe. 1995. A rapid and non-invasive selection of transgenic embryos before implantation using green fluorescent protein (GFP). FEBS Letters 375:125-128.
42. Cormack, B. 1998. Green fluorescent protein as a reporter of transcription and protein localization in fungi. Current Opinion in Microbiology 1:406-410.

The invention claimed is:

1. An isolated protein molecule comprising an amino acid sequence, wherein the amino acid sequence is at least 96% identical to the amino acid sequence of SEQ ID NO: 1 or wherein the amino acid sequence is encoded by a nucleic acid sequence that is at least 96% identical to the nucleic acid sequence of SEQ ID NO: 2, and wherein the isolated protein molecule has green fluorescent protein activity.

2. The protein molecule of claim 1, wherein the protein molecule has a molar extinction coefficient of at least 100,000 $M^{-1}cm^{-1}$.

3. The protein molecule of claim 1, wherein the protein molecule has a quantum yield of at least 0.90.

4. The protein molecule of claim 1, wherein the amino acid sequence is at least 97, 98 or 99% identical to the amino acid sequence of SEQ ID NO: 1 or wherein the amino acid sequence is encoded by a nucleic acid sequence that is at least 97, 98 or 99% identical to the nucleic acid sequence of SEQ ID NO: 2.

5. The protein molecule of claim 1, wherein the protein molecule has an absorbance maximum between 480-490 nm and an emission maximum between 500-511 nm.

6. The protein molecule of claim 1, wherein the protein molecule comprises the amino acid sequence of SEQ ID NO: 1 and is isolated from *Pontella mimocerami*.

7. A purified green fluorescent protein produced by ligating one or more amplified nucleic acids encoding a green fluorescent protein into a vector, wherein said one or more amplified nucleic acids have a nucleotide sequence with at least 96% sequence identity to the nucleotide sequence of SEQ ID NO: 2, and wherein the encoded green fluorescent protein has green fluorescent protein activity;

transfecting a host cell with the vector;

expressing the green fluorescent protein in the host cell; and purifying the green fluorescent protein from the host cell.

8. An isolated green fluorescent protein isolated by transfecting one or more cells with a nucleic acid encoding a green fluorescent protein, wherein said nucleic acid has a nucleotide sequence with at least 96% sequence identity to the nucleotide sequence of SEQ ID NO: 2 and wherein the green fluorescent protein has green fluorescent protein activity;

plating the one or more cells onto a culture plate;

incubating the culture plate at 37° C. for a period not less than 8 hours, to express said green fluorescent protein in the one or more cells and form one or more green fluorescent colonies;

selecting and picking at least one of the one or more green fluorescent colonies from the culture plate to form selected green fluorescent colonies;

resuspending the selected green fluorescent colonies in water or a buffer to form resuspended green fluorescent colonies;

plating the resuspended green fluorescent colonies onto a second culture plate;

incubating the second culture plate at room temperature for at least 48 hours to form green fluorescent colonies;

resuspending the green fluorescent colonies in the buffer;

sonicating the green fluorescent colonies in the buffer on ice to form a sonicated buffer solution;

centrifuging the sonicated buffer solution;

separating the sonicated buffer solution to yield a lysate and a cellular debris; and isolating said green fluorescent protein from the lysate, the cellular debris or both using metal-affinity chromatography, chromatography, affinity extraction, or other protein purification techniques.

9. A kit comprising one or more containers, wherein at least one of the one or more containers comprises an isolated protein molecule comprising an amino acid sequence, wherein the amino acid sequence is at least 96% identical to the amino acid sequence of SEQ ID NO: 1, and wherein the isolated protein molecule has green fluorescent protein activity.

* * * * *

SEQUENCE LISTING

<160> NUMBER OF SEQ ID NOS: 20

<210> SEQ ID NO 1
<211> LENGTH: 222
<212> TYPE: PRT
<213> ORGANISM: Pontella mimocerami

<400> SEQUENCE: 1

Met Pro Asn Met Lys Leu Glu Cys Arg Ile Ser Gly Thr Met Asn Gly
1               5                   10                  15

Glu Glu Phe Glu Leu Val Gly Asn Gly Asp Gly Asn Thr Asp Glu Gly
            20                  25                  30

Arg Met Thr Asn Lys Met Lys Ser Thr Lys Gly Pro Leu Ser Phe Ser

```
                35                  40                  45
    Pro Tyr Leu Leu Ser His Val Leu Gly Tyr Gly Tyr His Tyr Ala
        50                  55                  60

Thr Phe Pro Ala Gly Tyr Glu Asn Val Tyr Leu His Ala Met Lys Asn
    65                  70                  75                  80

Gly Gly Tyr Ser Asn Thr Arg Thr Glu Arg Tyr Glu Asp Gly Gly Ile
                    85                  90                  95

Ile Ser Ala Thr Phe Asn Tyr Arg Tyr Glu Gly Asp Lys Ile Ile Gly
                    100                 105                 110

Asp Phe Lys Val Val Gly Thr Gly Phe Pro Thr Asn Ser Ile Ile Phe
                115                 120                 125

Thr Asp Lys Ile Ile Lys Ser Asn Pro Thr Cys Glu His Ile Tyr Pro
            130                 135                 140

Lys Ala Asp Asn Ile Leu Val Asn Ala Tyr Thr Arg Thr Trp Met Leu
    145                 150                 155                 160

Arg Asp Gly Gly Tyr Tyr Ser Ala Gln Val Asn Asn His Met His Phe
                    165                 170                 175

Lys Ser Ala Ile His Pro Thr Met Leu Gln Asn Gly Gly Ser Met Phe
                    180                 185                 190

Thr Tyr Arg Lys Val Glu Glu Leu His Thr Gln Thr Glu Val Gly Ile
                195                 200                 205

Val Glu Tyr Gln His Val Phe Lys Thr Pro Thr Ala Phe Ala
            210                 215                 220

<210> SEQ ID NO 2
<211> LENGTH: 666
<212> TYPE: DNA
<213> ORGANISM: Pontella mimocerami

<400> SEQUENCE: 2
atgcccaaca tgaagcttga gtgccgcatc tccggaacca tgaacggaga ggagtttgaa    60
cttgttggta tggagatgg aaacactgat gagggacgca tgaccaacaa gatgaagtcc    120
accaagggac ctctctcctt ctctccctac ttgctctccc atgttcttgg ctatggatac    180
taccactatg ctaccttccc tgctggatat gaaaatgtct acctccatgc catgaagaat    240
ggaggttact ctaacacaag aactgagagg tatgaggatg gaggtatcat ttctgctacc    300
ttcaactaca gatatgaagg agacaagatc attgggact tcaaggttgt tggaactgga    360
ttccctacca acagcatcat cttcactgac aaaataatca gtccaaccc tacctgtgag    420 cacatctacc ccaaggctga caatattctt gtgaatgcct acaccagaac ctggatgctt    480
agagatggtg gatactactc tgctcaggtc aacaaccaca tgcacttcaa gagtgccatc    540
catcccacca tgctccagaa tggtggatcc atgttcacct acagaaaggt tgaggagctc    600
cacacacaaa ctgaagttgg tattgttgag taccagcatg tcttcaaaac tccaactgct    660
tttgct                                                              666

<210> SEQ ID NO 3
<211> LENGTH: 222
<212> TYPE: PRT
<213> ORGANISM: Pontella mimocerami

<400> SEQUENCE: 3

Met Pro Asn Met Lys Leu Glu Cys Arg Ile Ser Gly Thr Met Asn Gly
1               5                   10                  15

Glu Glu Phe Lys Leu Val Gly Ala Gly Glu Gly Asn Thr Asp Glu Gly
```

```
              20                  25                  30
Arg Met Thr Asn Lys Val Lys Ser Thr Lys Gly Pro Leu Pro Phe Ser
             35                  40                  45

Pro Tyr Leu Leu Ser His Val Leu Gly Tyr Gly Tyr His Tyr Ala
         50                  55                  60

Thr Phe Pro Ala Gly Tyr Glu Asn Val Tyr Leu His Ala Met Lys Asn
 65                  70                  75                  80

Gly Gly Tyr Ser Asn Thr Arg Thr Glu Arg Tyr Glu Asp Gly Gly Ile
                 85                  90                  95

Ile Ser Ala Thr Phe Asn Tyr Arg Tyr Glu Gly Asp Lys Ile Ile Gly
                100                 105                 110

Asp Phe Lys Val Val Gly Thr Gly Phe Pro Thr Asn Ser Ile Ile Phe
            115                 120                 125

Thr Asp Lys Ile Ile Lys Ser Asn Pro Thr Cys Glu His Ile Tyr Pro
            130                 135                 140

Lys Ala Asp Asn Ile Leu Val Asn Ala Tyr Thr Arg Thr Trp Met Leu
145                 150                 155                 160

Arg Asp Gly Gly Tyr Tyr Ser Ala Gln Val Asn Asn His Met His Phe
                165                 170                 175

Lys Ser Ala Ile His Pro Thr Met Leu Gln Asn Gly Gly Ser Met Phe
                180                 185                 190

Thr Tyr Arg Lys Val Glu Glu Leu His Thr Gln Thr Glu Val Gly Ile
                195                 200                 205

Val Glu Tyr Gln His Val Phe Lys Arg Pro Thr Ala Phe Ala
            210                 215                 220
```

<210> SEQ ID NO 4
<211> LENGTH: 666
<212> TYPE: DNA
<213> ORGANISM: Pontella mimocerami

<400> SEQUENCE: 4

```
atgcccaaca tgaagcttga gtgccgtatc tccggaacca tgaacggaga ggagtttaaa      60
cttgttggtg ctggagaagg aaacactgat gagggacgca tgaccaacaa ggtgaagtcc     120
accaagggac ctctcccctt ctctccctac ttgctctctc acgttcttgg ctatggatac     180
taccactatg ctaccttccc tgctggatat gaaaatgtct acctccatgc catgaagaat     240
ggaggttact ccaacaccag aactgagagg tatgaggacg gaggtatcat ttctgctacc     300
ttcaactaca gatatgaagg agacaagatc attggagact caaggttgtg tggaactgga     360
ttccccacca acagcatcat cttcactgac aagattatca gtccaaccc tacctgtgag     420
cacatatacc ccaaggctga caatattctt gtgaatgcct acaccagaac ctggatgctt     480
agagatggtg gatactactc tgctcaggtc aacaaccaca tgcacttcaa gagtgccatc     540
catcccacca tgctccagaa tggtggatcc atgttcacct acagaaaggt tgaggagctc     600
cacacacaaa ctgaagttgg tattgttgag taccagcatg tcttcaagag gccaactgct     660
tttgct                                                                666
```

<210> SEQ ID NO 5
<211> LENGTH: 222
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 5

```
Met Pro Asn Met Glu Leu Glu Cys Arg Ile Ser Gly Thr Met Asn Gly
1               5                   10                  15
Glu Glu Phe Glu Leu Val Gly Asn Gly Asp Gly Asn Thr Asp Glu Gly
            20                  25                  30
Arg Met Thr Asn Lys Met Lys Ser Thr Lys Gly Pro Leu Ser Phe Ser
        35                  40                  45
Pro Tyr Leu Leu Ser His Val Leu Gly Tyr Gly Tyr Tyr His Tyr Ala
50                  55                  60
Thr Phe Pro Ala Gly Tyr Glu Asn Val Tyr Leu His Ala Met Lys Asn
65                  70                  75                  80
Gly Gly Tyr Ser Asn Thr Arg Thr Glu Arg Tyr Glu Asp Gly Gly Ile
                85                  90                  95
Ile Ser Ala Thr Phe Asn Tyr Arg Tyr Glu Gly Asp Lys Ile Ile Gly
            100                 105                 110
Asp Phe Lys Val Val Gly Thr Gly Phe Pro Thr Asn Ser Ile Ile Phe
        115                 120                 125
Thr Asp Lys Ile Ile Lys Ser Asn Pro Thr Cys Glu His Ile Tyr Pro
130                 135                 140
Lys Ala Asp Asn Ile Leu Val Asn Ala Tyr Thr Arg Thr Trp Met Leu
145                 150                 155                 160
Arg Asp Gly Gly Tyr Tyr Ser Ala Gln Val Asn Asn His Met His Phe
                165                 170                 175
Lys Ser Ala Ile His Pro Thr Met Leu Gln Asn Gly Gly Ser Met Phe
            180                 185                 190
Thr Tyr Arg Lys Val Glu Glu Leu His Thr Gln Thr Glu Val Gly Ile
        195                 200                 205
Val Glu Tyr Gln His Val Phe Lys Thr Pro Thr Ala Phe Ala
210                 215                 220
```

<210> SEQ ID NO 6
<211> LENGTH: 666
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 6

```
atgcccaaca tggagcttga gtgccgcatc tccggaacca tgaacggaga ggagtttgaa      60
cttgttggta tggagatgg aaacactgat gagggacgca tgaccaacaa gatgaagtcc      120
accaagggac tctctcctt ctctccctac ttgctctccc atgttcttgg ctatggatac      180
taccactatg ctaccttccc tgctggatat gaaaatgtct acctccatgc catgaagaat      240
ggaggttact ctaacacaag aactgagagg tatgaggatg aggtatcat ttctgctacc      300
ttcaactaca gatatgaagg agacaagatc attgggact tcaaggttgt tggaactgga      360
ttccctacca acagcatcat cttcactgac aaaataatca gtccaaccc tacctgtgag      420
cacatctacc ccaaggctga caatattctt gtgaatgcct acaccagaac ctggatgctt      480
agagatggtg gatactactc tgctcaggtc aacaaccaca tgcacttcaa gagtgccatc      540
catcccacca tgctccagaa tggtggatcc atgttcacct acagaaaggt tgaggagctc      600
cacacacaaa ctgaagttgg tattgttgag taccagcatg tcttcaaaac tccaactgct      660
tttgct                                                                 666
```

<210> SEQ ID NO 7
<211> LENGTH: 222
<212> TYPE: PRT
<213> ORGANISM: Artificial Sequence
<220> FEATURE:
<223> OTHER INFORMATION: Description of Artificial Sequence: Synthetic amino acid sequence

<400> SEQUENCE: 7

```
Met Pro Asn Met Thr Leu Glu Ser Ala Ile Ser Gly Thr Met Asn Gly
1               5                   10                  15

Glu Glu Phe Glu Leu Val Gly Asn Gly Asp Gly Asn Thr Asp Glu Gly
            20                  25                  30

Arg Met Thr Asn Lys Met Lys Ser Thr Lys Gly Pro Leu Ser Phe Ser
        35                  40                  45

Pro Tyr Leu Leu Ser His Val Leu Gly Tyr Gly Tyr Tyr His Tyr Ala
    50                  55                  60

Thr Phe Pro Ala Gly Tyr Glu Asn Val Tyr Leu His Ala Met Lys Asn
65                  70                  75                  80

Gly Gly Tyr Ser Asn Thr Arg Thr Glu Arg Tyr Glu Asp Gly Gly Ile
                85                  90                  95

Ile Ser Ala Thr Phe Asn Tyr Arg Tyr Glu Gly Asp Lys Ile Ile Gly
            100                 105                 110

Asp Phe Lys Val Val Gly Thr Gly Phe Pro Thr Asn Ser Ile Ile Phe
        115                 120                 125

Thr Asp Lys Ile Ile Lys Ser Asn Pro Thr Cys Glu His Ile Tyr Pro
    130                 135                 140

Lys Ala Asp Asn Ile Leu Val Asn Ala Tyr Thr Arg Thr Trp Met Leu
145                 150                 155                 160

Arg Asp Gly Gly Tyr Tyr Ser Ala Gln Val Asn Asn His Met His Phe
                165                 170                 175

Lys Ser Ala Ile His Pro Thr Met Leu Gln Asn Gly Gly Ser Met Phe
            180                 185                 190

Thr Tyr Arg Lys Val Glu Glu Leu His Thr Gln Thr Glu Val Gly Ile
        195                 200                 205

Val Glu Tyr Gln His Val Phe Lys Thr Pro Thr Ala Phe Ala
    210                 215                 220
```

<210> SEQ ID NO 8
<211> LENGTH: 666
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 8

```
atgcccaaca tgacgcttga gtccgccatc tccggaacca tgaacggaga ggagtttgaa      60
cttgttggta tggagatgg aaacactgat gaggacgca tgaccaacaa gatgaagtcc       120
accaagggac tctctcctt ctctcccctac ttgctctccc atgttcttgg ctatggatac     180
taccactatg ctaccttccc tgctggatat gaaaatgtct acctccatgc catgaagaat     240
ggaggttact ctaacacaag aactgagagg tatgaggatg gaggtatcat ttctgctacc     300
ttcaactaca gatatgaagg agacaagatc attggggact tcaaggttgt tggaactgga    360
ttccctacca acagcatcat cttcactgac aaaataatca gtccaacccc tacctgtgag    420
cacatctacc ccaaggctga caatattctt gtgaatgcct acaccagaac ctggatgctt    480
```

```
agagatggtg gatactactc tgctcaggtc aacaaccaca tgcacttcaa gagtgccatc    540
catcccacca tgctccagaa tggtggatcc atgttcacct acagaaaggt tgaggagctc    600
cacacacaaa ctgaagttgg tattgttgag taccagcatg tcttcaaaac tccaactgct    660
tttgct                                                              666
```

```
<210> SEQ ID NO 9
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
aagcagtggt atcaacgcag agtcgcagtc ggtactv                              37

<210> SEQ ID NO 10
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
agtggactat ccatgaacgc aaagcagtgg tatcaacgca gagt                      44

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
ttgattgatt gaaggagaaa tatcatg                                         27

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
catcaccatc accatcacta aa                                              22

<210> SEQ ID NO 13
<211> LENGTH: 238
<212> TYPE: PRT
<213> ORGANISM: Aquorea victoria

<400> SEQUENCE: 13
```

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe

Ser Tyr Gly Val Gln Cys Phe Ser Arg Tyr Pro Asp His Met Lys Gln
 65                  70                  75                  80

His Asp Phe Phe Lys Ser Ala Met Pro Glu Gly Tyr Val Gln Glu Arg
                 85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235

<210> SEQ ID NO 14
<211> LENGTH: 220
<212> TYPE: PRT
<213> ORGANISM: Calliostoma poppei

<400> SEQUENCE: 14

Met Thr Thr Phe Lys Ile Glu Ser Arg Ile His Gly Asn Leu Asn Gly
1               5                   10                  15

Glu Lys Phe Glu Leu Val Gly Gly Gly Val Gly Glu Glu Gly Arg Leu
            20                  25                  30

Glu Ile Glu Met Lys Thr Lys Asp Lys Pro Leu Ala Phe Ser Pro Phe
        35                  40                  45

Leu Leu Ser His Cys Met Gly Tyr Gly Phe Tyr His Phe Ala Ser Phe
    50                  55                  60

Pro Lys Gly Thr Lys Asn Ile Tyr Leu His Ala Ala Thr Asn Gly Gly
65                  70                  75                  80

Tyr Thr Asn Thr Arg Lys Glu Ile Tyr Glu Asp Gly Gly Ile Leu Glu
                85                  90                  95

Val Asn Phe Arg Tyr Thr Tyr Thr Glu Phe Asn Lys Ile Ile Gly Asp
            100                 105                 110

Val Glu Cys Ile Gly His Gly Phe Pro Ser Gln Ser Pro Ile Phe Lys
        115                 120                 125

Asp Thr Ile Val Lys Ser Cys Pro Thr Val Asp Leu Met Leu Pro Met
    130                 135                 140

Ser Gly Asn Ile Ile Ala Ser Ser Tyr Ala Arg Ala Phe Gln Leu Lys
145                 150                 155                 160

Asp Gly Ser Phe Tyr Thr Ala Glu Val Lys Asn Asn Ile Asp Phe Lys
                165                 170                 175

Asn Pro Ile His Glu Ser Phe Ser Lys Ser Gly Pro Met Phe Thr His
            180                 185                 190

Arg Arg Val Glu Glu Thr His Thr Lys Glu Asn Leu Ala Met Val Glu
            195                 200                 205

Tyr Gln Gln Val Phe Asn Ser Ala Pro Arg Asp Met
    210                 215                 220

<210> SEQ ID NO 15
<211> LENGTH: 222
<212> TYPE: PRT
<213> ORGANISM: Labidocera aestiva

<400> SEQUENCE: 15

Met Pro Val Met Lys Ile Glu Cys Arg Ile Ser Gly Thr Met Asn Gly
1               5                   10                  15

Glu Glu Phe Glu Leu Val Gly Ala Gly Asp Gly Asn Thr Asp Glu Gly
            20                  25                  30

Arg Met Thr Asn Lys Met Lys Ser Thr Lys Gly Pro Leu Ser Phe Ser
        35                  40                  45

Pro Tyr Leu Leu Ser His Ile Met Gly Tyr Gly Phe Tyr His Tyr Ala
    50                  55                  60

Thr Phe Pro Ala Gly Tyr Glu Asn Val Tyr Leu His Ala Ala Lys Asn
65                  70                  75                  80

Gly Gly Tyr Thr Asn Thr Arg Thr Glu Arg Tyr Glu Asp Gly Gly Ile
                85                  90                  95

Ile Ser Val Asn Phe Thr Tyr Arg Tyr Glu Gly Asn Lys Val Ile Gly
            100                 105                 110

Asp Phe Lys Val Val Gly Ser Gly Phe Pro Ala Asn Ser Val Ile Phe
        115                 120                 125

Thr Asp Lys Ile Ile Lys Ser Asn Pro Thr Cys Glu His Ile Tyr Pro
    130                 135                 140

Lys Gly Asp Asn Ile Leu Val Asn Ala Tyr Thr Arg Thr Trp Met Leu
145                 150                 155                 160

Arg Asp Gly Gly Tyr Tyr Ser Ala Gln Val Asn Asn His Leu His Phe
                165                 170                 175

Lys Thr Ala Met His Pro Thr Met Leu Gln Asn Gly Gly Ser Met Phe
            180                 185                 190

Thr Tyr Arg Lys Val Glu Glu Leu His Ser Gln Ser Asp Val Gly Ile
        195                 200                 205

Val Glu Tyr Gln His Val Phe Lys Thr Pro Thr Ala Phe Ala
    210                 215                 220

<210> SEQ ID NO 16
<211> LENGTH: 222
<212> TYPE: PRT
<213> ORGANISM: unidentified Pontella

<400> SEQUENCE: 16

Met Ala Ala Met Lys Ile Glu Cys Arg Ile Thr Gly Thr Met Asn Gly
1               5                   10                  15

Val Glu Phe Glu Leu Val Gly Gly Gly Glu Gly Asn Thr Asp Gln Gly
            20                  25                  30

Arg Met Thr Asn Lys Met Lys Ser Thr Lys Gly Pro Leu Ser Phe Ser
        35                  40                  45

Pro Tyr Leu Leu Ser His Val Met Gly Tyr Gly Phe Tyr His Phe Gly
    50                  55                  60

Thr Phe Pro Ser Gly Tyr Glu Asn Pro Tyr Val His Ala Met Thr Asn
65                  70                  75                  80

```
Gly Gly Tyr Thr Asn Thr Arg Ile Glu Ser Tyr Glu Asp Gly Gly Val
                85                  90                  95

Leu Tyr Leu Thr Phe Asn Tyr Arg Leu Asp Gly Asn Lys Ile Ile Gly
            100                 105                 110

Asp Phe Lys Cys Val Gly Thr Gly Phe Pro Glu Asp Ser Val Ile Phe
            115                 120                 125

Thr Asp Lys Ile Ile Lys Ser Asn Pro Asn Cys Glu His Phe Tyr Pro
130                 135                 140

Met Ala Glu Asn Ile Met Lys Asn Ala Tyr Met Arg Thr Leu Ser Leu
145                 150                 155                 160

Arg Asp Gly Gly Tyr Tyr Ser Gly Gln Val Thr Ser His Ile His Phe
            165                 170                 175

Lys Asn Ala Ile His Pro Ser Ile Leu His Asn Gly Gly Ser Met Phe
            180                 185                 190

Thr Tyr Arg Arg Val Glu Glu Leu His Thr Gln Thr Asp Leu Gly Ile
            195                 200                 205

Val Glu Tyr Gln His Val Phe Lys Thr Pro Thr Ala Phe Ala
            210                 215                 220

<210> SEQ ID NO 17
<211> LENGTH: 222
<212> TYPE: PRT
<213> ORGANISM: Plantago meadi

<400> SEQUENCE: 17

Met Pro Asp Met Lys Leu Glu Cys His Ile Ser Gly Thr Met Asn Gly
1               5                   10                  15

Glu Glu Phe Glu Leu Ile Gly Ala Gly Asp Gly Asn Thr Asp Glu Gly
            20                  25                  30

Arg Met Thr Asn Lys Met Lys Ser Ile Lys Gly Pro Ile Ser Phe Ser
            35                  40                  45

Pro Tyr Leu Leu Ser His Ile Leu Gly Tyr Gly Tyr Tyr His Phe Ala
        50                  55                  60

Thr Phe Pro Ala Gly Tyr Glu Asn Ile Tyr Leu His Ala Met Lys Asn
65                  70                  75                  80

Gly Gly Tyr Ser Asn Val Arg Thr Glu Arg Tyr Glu Asp Gly Gly Ile
            85                  90                  95

Ile Ser Ile Thr Phe Asn Tyr Tyr Glu Gly Asn Lys Ile Ile Gly
            100                 105                 110

Asp Phe Lys Val Val Gly Thr Gly Phe Pro Thr Asn Ser Leu Ile Phe
            115                 120                 125

Thr Asp Lys Ile Ile Lys Ser Asn Pro Thr Cys Glu Asn Met Phe Pro
130                 135                 140

Lys Ala Asp Asn Thr Leu Val Asn Ala Tyr Thr Arg Thr Tyr Leu Leu
145                 150                 155                 160

Lys Asp Gly Gly Tyr Tyr Ser Ala Gln Val Asn Asn His Met His Phe
            165                 170                 175

Lys Ser Ala Ile His Thr Thr Met Leu Gln Asn Gly Gly Ser Met Phe
            180                 185                 190

Thr Tyr Arg Val Val Glu Glu Thr His Thr Gln Asn Glu Val Ala Ile
            195                 200                 205

Val Glu Tyr Gln Asn Val Phe Lys Thr Pro Thr Ala Phe Ala
            210                 215                 220

<210> SEQ ID NO 18
```

```
<211> LENGTH: 222
<212> TYPE: PRT
<213> ORGANISM: Plantago meadi

<400> SEQUENCE: 18

Met Pro Asp Met Lys Leu Glu Cys His Ile Ser Gly Thr Met Asn Gly
1               5                   10                  15

Glu Glu Phe Glu Leu Ile Gly Ser Gly Asp Gly Asn Thr Asp Gln Gly
            20                  25                  30

Arg Met Thr Asn Asn Met Lys Ser Ile Lys Gly Pro Leu Ser Phe Ser
        35                  40                  45

Pro Tyr Leu Leu Ser His Ile Leu Gly Tyr Gly Tyr Tyr His Phe Ala
    50                  55                  60

Thr Phe Pro Ala Gly Tyr Glu Asn Ile Tyr Leu His Ala Met Lys Asn
65                  70                  75                  80

Gly Gly Tyr Ser Asn Val Arg Thr Glu Arg Tyr Glu Asp Gly Gly Ile
                85                  90                  95

Ile Ser Ile Thr Phe Asn Tyr Arg Tyr Glu Gly Ser Lys Ile Ile Gly
            100                 105                 110

Asp Phe Lys Val Ile Gly Thr Gly Phe Pro Thr Asp Ser Leu Ile Phe
        115                 120                 125

Thr Asp Lys Ile Ile Lys Ser Asn Pro Thr Cys Glu Asn Met Phe Pro
130                 135                 140

Lys Ala Asp Asn Ile Leu Val Asn Ala Tyr Thr Arg Thr Tyr Leu Leu
145                 150                 155                 160

Lys Asp Gly Gly Tyr Tyr Ser Ala Gln Val Asn Asn His Met His Phe
                165                 170                 175

Lys Ser Ala Ile His Pro Thr Met Leu Gln Asn Gly Gly Ser Met Phe
            180                 185                 190

Thr His Arg Val Val Glu Glu Asn His Thr Lys Thr Asn Val Ala Ile
        195                 200                 205

Val Glu Tyr Gln Asn Val Phe Lys Thr Pro Thr Ala Phe Ala
    210                 215                 220

<210> SEQ ID NO 19
<211> LENGTH: 222
<212> TYPE: PRT
<213> ORGANISM: Pseudopontella plumata

<400> SEQUENCE: 19

Met Pro Ala Met Lys Ile Glu Cys Arg Ile Ser Gly Thr Leu Asn Gly
1               5                   10                  15

Val Val Phe Glu Leu Val Gly Gly Gly Glu Gly Ile Pro Glu Gln Gly
            20                  25                  30

Arg Met Thr Asn Lys Met Lys Ser Thr Lys Gly Ala Leu Thr Phe Ser
        35                  40                  45

Pro Tyr Leu Leu Ser His Val Met Gly Tyr Gly Phe Tyr His Phe Gly
    50                  55                  60

Thr Tyr Pro Ser Gly Tyr Glu Asn Pro Phe Leu His Ala Ala Asn Asn
65                  70                  75                  80

Gly Gly Tyr Thr Asn Thr Arg Ile Glu Lys Tyr Glu Asp Gly Gly Val
                85                  90                  95

Leu His Val Ser Phe Ser Tyr Arg Tyr Glu Ala Gly Arg Val Ile Gly
            100                 105                 110

Asp Phe Lys Val Val Gly Thr Gly Phe Pro Glu Asp Ser Val Ile Phe
        115                 120                 125
```

```
Thr Asp Lys Ile Ile Arg Ser Asn Ala Thr Val Glu His Leu His Pro
    130                 135                 140

Met Gly Asp Asn Val Leu Val Gly Ser Phe Ala Arg Thr Phe Ser Leu
145                 150                 155                 160

Arg Asp Gly Gly Tyr Tyr Ser Phe Val Val Asp Ser His Met His Phe
                165                 170                 175

Lys Ser Ala Ile His Pro Ser Ile Leu Gln Asn Gly Gly Ser Met Phe
                180                 185                 190

Ala Phe Arg Arg Val Glu Glu Leu His Ser Asn Thr Glu Leu Gly Ile
        195                 200                 205

Val Glu Tyr Gln His Ala Phe Lys Thr Pro Thr Ala Phe Ala
    210                 215                 220

<210> SEQ ID NO 20
<211> LENGTH: 222
<212> TYPE: PRT
<213> ORGANISM: Pseudopontella plumata

<400> SEQUENCE: 20

Met Pro Ala Met Lys Ile Glu Cys Arg Ile Thr Gly Thr Leu Asn Gly
1               5                   10                  15

Val Glu Phe Glu Leu Val Gly Gly Gly Glu Gly Thr Pro Glu Gln Gly
                20                  25                  30

Arg Met Thr Asn Lys Met Lys Ser Thr Lys Gly Ala Leu Thr Phe Ser
                35                  40                  45

Pro Tyr Leu Leu Ser His Val Met Gly Tyr Gly Phe Tyr His Phe Gly
    50                  55                  60

Thr Tyr Pro Ser Gly Tyr Glu Asn Pro Phe Leu His Ala Ile Asn Asn
65                  70                  75                  80

Gly Gly Tyr Thr Asn Thr Arg Ile Glu Lys Tyr Glu Asp Gly Gly Val
                85                  90                  95

Leu His Val Ser Phe Ser Tyr Arg Tyr Glu Ala Gly Arg Val Ile Gly
                100                 105                 110

Asp Phe Lys Val Val Gly Thr Gly Phe Pro Glu Asp Ser Val Ile Phe
            115                 120                 125

Thr Asp Lys Ile Ile Arg Ser Asn Ala Thr Val Glu His Leu His Pro
    130                 135                 140

Met Gly Asp Asn Val Leu Val Gly Ser Phe Ala Arg Thr Phe Ser Leu
145                 150                 155                 160

Arg Asp Gly Gly Tyr Tyr Ser Phe Val Val Asp Ser His Met His Phe
                165                 170                 175

Lys Ser Ala Ile His Pro Ser Ile Leu Gln Asn Gly Gly Pro Met Phe
                180                 185                 190

Ala Phe Arg Arg Val Glu Glu Leu His Ser Asn Thr Glu Leu Gly Ile
        195                 200                 205

Val Glu Tyr Gln His Ala Phe Lys Thr Pro Ile Ala Phe Ala
    210                 215                 220
```